(12) United States Patent
Fischer et al.

(10) Patent No.: US 12,702,559 B2
(45) Date of Patent: Aug. 11, 2026

(54) CUTTING AND BENDING TOOL FOR PELVIC IMPLANTS

(71) Applicant: WALDEMAR LINK GMBH & CO. KG, Hamburg (DE)

(72) Inventors: Hans-Joachim Fischer, Norderstedt (DE); Klaus Dmuschewsky, Hamburg (DE)

(73) Assignee: WALDEMAR LINK GMBH & CO. KG, Hamburg (DE)

( * ) Notice: Subject to any disclaimer, the term of this patent is extended or adjusted under 35 U.S.C. 154(b) by 398 days.

(21) Appl. No.: 18/356,119

(22) Filed: Jul. 20, 2023

(65) Prior Publication Data

US 2024/0024114 A1 Jan. 25, 2024

Related U.S. Application Data

(60) Provisional application No. 63/369,208, filed on Jul. 22, 2022.

(51) Int. Cl.

| | |
|---|---|
| ***A61F 2/30*** | (2006.01) |
| ***A61L 2/18*** | (2026.01) |
| ***A61L 2/26*** | (2006.01) |

(52) U.S. Cl.

CPC ............ *A61F 2/30942* (2013.01); *A61L 2/18* (2013.01); *A61L 2/26* (2013.01); *A61F 2002/3096* (2013.01)

(58) Field of Classification Search

CPC ............ A61B 17/8066; A61B 17/8085; A61B 17/8863; A61B 2050/3011; A61B 50/20;

(Continued)

(56) References Cited

U.S. PATENT DOCUMENTS

| | | | | |
|---|---|---|---|---|
| 6,644,087 B1 * | 11/2003 | Ralph | ................ | A61B 17/8863 72/213 |
| 2012/0186411 A1 * | 7/2012 | Lodahi | ............... | A61B 17/8863 83/639.1 |
| 2017/0209198 A1 | 7/2017 | Rinner | | |

FOREIGN PATENT DOCUMENTS

| | | |
|---|---|---|
| CN | 106236239 A | 12/2016 |
| CN | 213697159 U | 7/2021 |

(Continued)

OTHER PUBLICATIONS

Zimmer Biomet, “Instrument Disassembly and Assembly Manual”, Retrieved from the Internet: URL:https://www.zimmerbiomet.eu/content/da m/zimmer-biomet/medical-professionals/supp ort/instrument-reprocessing/1258.4-GLBL-en -Disassembly-Guide-digital; 2021, pp. 1-128.

(Continued)

*Primary Examiner* — Mohamed G Gabr
(74) *Attorney, Agent, or Firm* — Chiesa Shahinian & Giantomasi PC

(57) ABSTRACT

A modification device, and methods of using and methods involving the same are provided. The modification device includes a base configured to contact a supporting surface; a handle configured to receive a force and configured to provide a modification force to a modification tool; and the modification tool between the handle and the base, wherein the modification tool is configured to receive the modification force and configured to provide the modification force to a portion of an implant.

20 Claims, 24 Drawing Sheets

(58) Field of Classification Search
CPC ................. A61B 50/33; A61F 2/30942; A61F 2002/30578; A61F 2002/3096; A61F 2002/3408; A61F 2002/3432; A61L 2/18; A61L 2/26
See application file for complete search history.

(56) References Cited

FOREIGN PATENT DOCUMENTS

| | | |
|---|---|---|
| DE | 9105152 U1 | 9/1991 |
| JP | 6902130 B1 | 7/2021 |

OTHER PUBLICATIONS

Extended European Search Report mailed Nov. 23, 2023, in connection with European Patent Application No. 23187130.2, filed Jul. 22, 2023, 9 pgs.
Communication pursuant to Article 94(3) EPC mailed Jun. 5, 2026, in connection with European Patent Application No. 23187130.2, 7 pgs.

* cited by examiner

CUTTING AND BENDING TOOL FOR PELVIC IMPLANTS

CROSS-REFERENCE TO RELATED APPLICATIONS

This application claims the benefit of U.S. Provisional Application No. 63/369,208, filed on Jul. 22, 2022; the disclosure of which is incorporated herein by reference in its entirety.

BACKGROUND

Individuals suffering from various skeletal or joint disorders often require the implantation of a prostheses in or on a bone. In cases of damage or injury to a hip joint, for example, implantation of a prosthetic acetabulum is often performed by an orthopedic surgeon.

Hip joints may suffer degeneration through disease or through wear. Hip joint endoprostheses have proven useful for therapy. These comprise a femoral component, which is implanted at the upper end of the thigh bone, and a hip component, which interacts with the femoral component and is implanted in the pelvic bone (acetabulum). In many cases, it can happen that the pelvic bone is damaged in the region of the hip joint. This has the effect of making it difficult to fasten the hip joint component to the pelvic bone. This is especially true of implants that function as a partial replacement of the pelvis. These have additional fastening elements in order not only to achieve secure anchoring of the joint socket of the hip joint implant on the pelvic bone, but also to stabilize the pelvic bone itself.

Some hip joint implants have a plurality of fastening elements on a support body that comprises the actual joint socket. These fastening elements comprise elongate brackets which extend in a cranial direction and which are provided with a plurality of drilled holes to permit fastening by means of a bone screw. They serve to securely fasten and stabilize the implant, and in particular the joint socket thereof, on a damaged pelvic bone.

Certain pelvic implants, such as prosthetic acetabulum, are designed to be adjustable and modifiable to the individual bone structure of a particular patient before and during surgical implantation. Access to the area of the implant is often required to ensure accurate modification of the implant. As such, adjustments to the implant are often performed in the operating room while the surgery is in progress and access to the implant area is readily available.

These adjustments can be performed by a tool designed to cut or modify the implant. Surgical instruments, particularly those used within an operating room, must be sterilized before use to prevent or reduce contamination. Thus, is it advantageous for such tools and instruments to be configured to be relatively easily sterilized between uses.

Accordingly, a device for adjusting, modifying, bending, and shaping a pelvic implant that is also configured to be sterilized is advantageous.

BRIEF SUMMARY OF THE DISCLOSURE

In accordance with one or more embodiments, devices and methods are provided.

In one embodiment a modification device is provided. The modification device comprises a base configured to contact a supporting surface; a handle configured to receive a force and configured to provide a modification force to a modification tool; and the modification tool between the handle and the base, wherein the modification tool is configured to receive the modification force and configured to provide the modification force to a portion of an implant.

In another embodiment a method of modifying a portion of an implant is provided. The method comprises placing a portion of the implant through a modification opening of a modification device; and moving a handle of the modification device to provide a modification force to a portion of an implant.

In another embodiment a method of sterilizing a modification device is provided. The method comprises removing the modification tool from between the handle and the base; removing the handle from the modification device; separating the base into two base pieces; placing the modification tool, the handle, and the base pieces into a sterilization basket; and exposing the modification tool, the handle, base pieces and the sterilization basket to a sterilizing procedure.

These and other advantages of the disclosure will be apparent to those of ordinary skill in the art by reference to the following detailed description and the accompanying drawings.

BRIEF DESCRIPTION OF THE DRAWINGS

The accompanying drawings, which are incorporated in and constitute a part of this specification, illustrate embodiments of the disclosure, and, together with the summary given above, and the detailed description of the embodiments below, serve as a further explanation and disclosure to explain and/or illustrate embodiments of the disclosure.

DETAILED DESCRIPTION

Figure 1A:
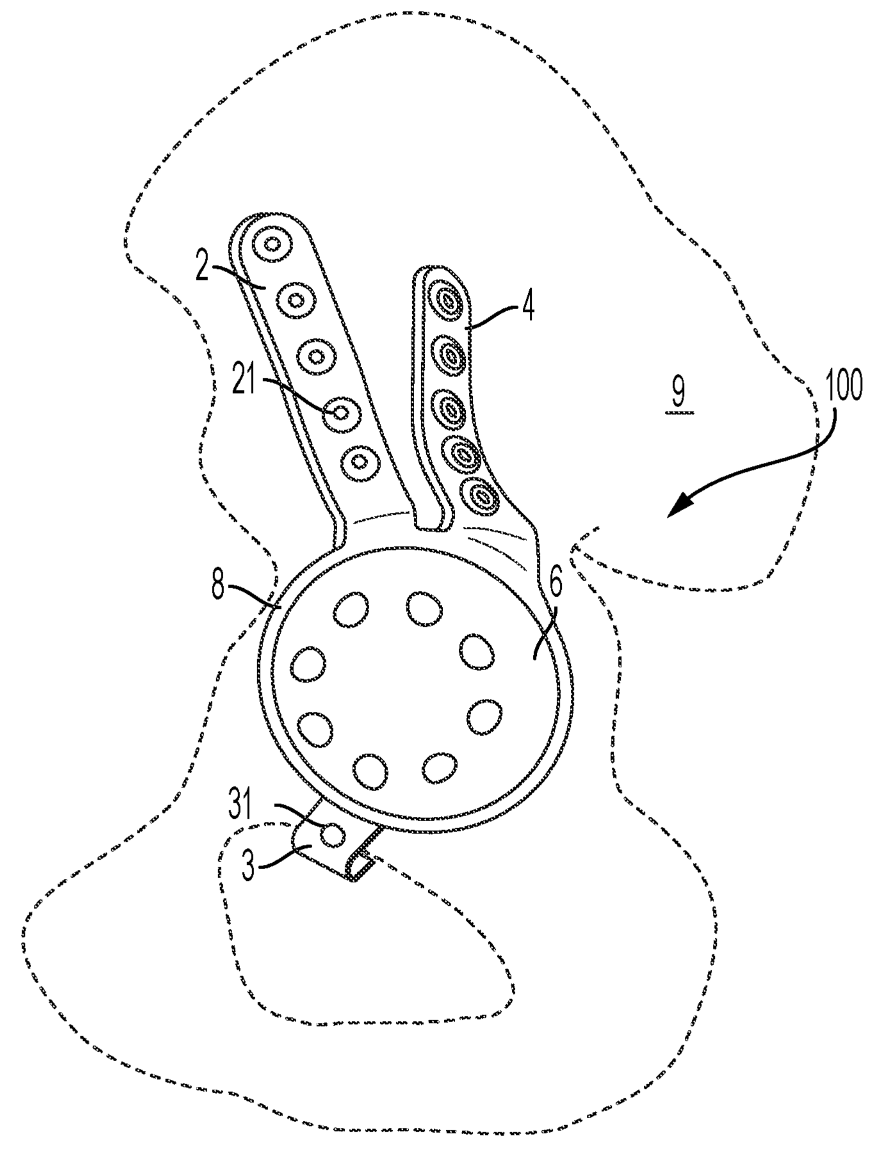
FIG. 1A shows an illustrative embodiment of the hip joint implant in the state when fitted on a pelvic bone.

It is noted that the drawings of the present application are provided for illustrative purposes only and, as such, the drawings are not drawn to scale. It is also noted that like and corresponding elements are referred to by like reference numerals.

In the following description, numerous specific details are set forth, such as particular structures, components, materials, dimensions, processing steps and techniques, in order to provide an understanding of the various embodiments of the present application. However, it will be appreciated by one of ordinary skill in the art that various embodiments of the present application may be practiced without these specific details. In other instances, well-known structures or processing steps have not been described in detail in order to avoid obscuring the present application.

As used herein, the term "substantially" or "substantial", is equally applicable when used in a negative connotation to refer to the complete or near complete lack of an action, characteristic, property, state, structure, item, or result. For example, a surface that is "substantially" flat would either be completely at, or so nearly flat that the effect would be the same as if it were completely flat.

As used herein, terms defined in the singular are intended to include those terms defined in the plural and vice versa.

As used in this specification and its appended claims, terms such as "a", "an" and "the" are not intended to refer to only a singular entity, but include the general class of which a specific example may be used for illustration, unless the context dictates otherwise. The terminology herein is used to describe specific embodiments of the disclosure, but their usage does not delimit the disclosure, except as outlined in the claims.

Unless otherwise indicated, all numbers expressing quantities of ingredients, properties such as molecular weights, reaction conditions, and so forth as used in the specification and claims are to be understood as being modified in all instances by the term "about." Accordingly, unless indicated to the contrary, the numerical parameters in the specification and claims are approximations that may vary depending upon the desired properties sought to be obtained by the present disclosure. At the very least, and without limiting the application of the doctrine of equivalents to the scope of the claims, each numerical parameter should at least be construed in light of the number of reported significant digits and by applying ordinary rounding techniques. Notwithstanding that the numerical ranges and parameters describing the broad scope of the disclosure are approximations, the numerical values in the specific examples are reported as precisely as possible. Any numerical value, however, inherently contains standard deviations that necessarily result from the errors found in the numerical value's testing measurements.

Thus, reference herein to any numerical range expressly includes each numerical value (including fractional numbers and whole numbers) encompassed by that range. To illustrate, reference herein to a range of "at least 50" or "at least about 50" includes whole numbers of 50, 51, 52, 53, 54, 55, 56, 57, 58, 59, 60, etc., and fractional numbers 50.1, 50.2 50.3, 50.4, 50.5, 50.6, 50.7, 50.8, 50.9, etc. In a further illustration, reference herein to a range of "less than 50" or "less than about 50" includes whole numbers 49, 48, 47, 46, 45, 44, 43, 42, 41, 40, etc., and fractional numbers 49.9, 49.8, 49.7, 49.6, 49.5, 49.4, 49.3, 49.2, 49.1, 49.0, etc. In yet another illustration, reference herein to a range of from "5 to 10" includes whole numbers of 5, 6, 7, 8, 9, and 10, and fractional numbers 5.1, 5.2, 5.3, 5.4, 5.5, 5.6, 5.7, 5.8, 5.9, etc.

In the discussion and claims herein, the term "about" indicates that the value listed may be somewhat altered, as long as the alteration does not result in nonconformance of the process or structure to the illustrated embodiment. For example, for some elements the term "about" can refer to a variation of ±0.1%, for other elements, the term "about" can refer to a variation of ±1% or ±10%, or any point therein.

Reference now will be made in detail to embodiments of the disclosure. It will be apparent to those skilled in the art that various modifications and variations can be made in the present disclosure without departing from the scope or spirit of the disclosure. For instance, features illustrated or described as part of one embodiment can be used on another embodiment to yield a still further embodiment.

An illustrative embodiment of a hip joint implant according to an embodiment of the disclosure is shown in FIG. 1A in a state when fitted on a pelvic bone 9 (acetabulum).

In this embodiment, the hip joint implant is designated as a whole by reference number 100 and comprises a socket-like support body 6 on which two flat and elongate fastening brackets 2 and 4 are arranged pointing upward (cranially). The implant 100 is one example of an implant of the present disclosure, in other embodiments, any other component that is configured to be implanted into a patient can be interacted with according to the described methods and devices. A shorter caudal flange 3, extending downward (caudally), is provided on the opposite side of the socket-like support body 6 (in the following also called socket for short). The size, shape and orientation of the fastening brackets 2 and 4, as well as the caudal flange 3, are just one example.

In the illustrative embodiment shown, the implant 100 is composed of two components, a socket 6 and a fastening component, which comprises the fastening brackets 2 and 4, the caudal flange 3 and a fastening ring 8, on which the fastening brackets 2, 4, and caudal flange 3 are arranged. In other embodiments, each of these components can be a different size and/or be at a different orientation as compared to the other components about the fastening ring 8.

In FIG. 1A, the fastening brackets 2 and 4 are each substantially elongate, substantially flat elements that are provided with a plurality of openings 21 configured to receive fastening means. The fastening caudal flange 3 is a substantially flat element, but, in the illustrative embodiment shown, it is shorter and wider than the fastening brackets 2. This embodiment is only an example; the disclosure is not limited thereto. The caudal flange 3 is likewise provided with a plurality of openings 31 configured to receive fastening means. The openings 21, 31, as well as the body openings 41, are designed as through-openings configured to receive fastening means (not shown). Screws, such as bone screws are one example of fastening means, however, any surgical fastening device can be used.

Figure 1B:
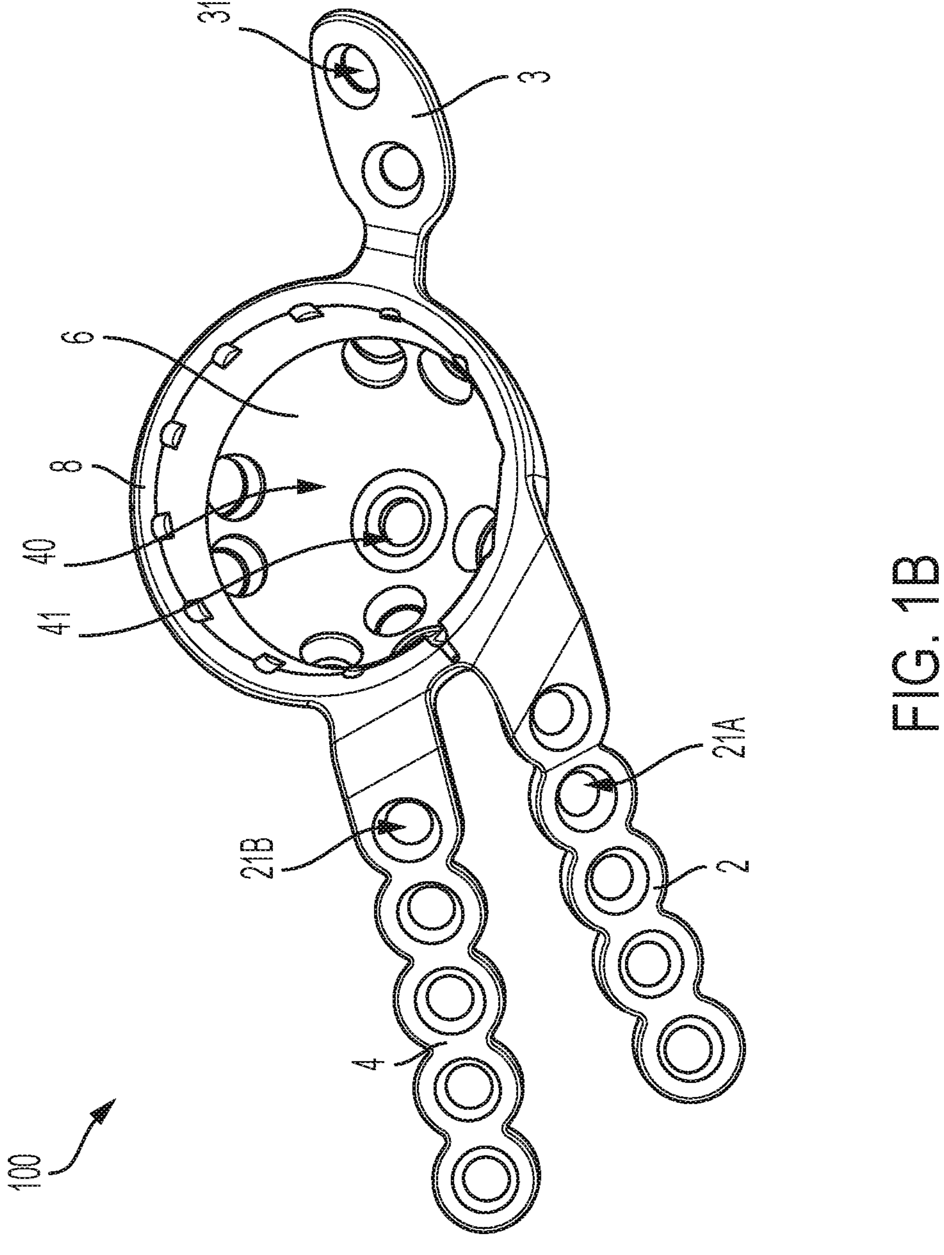
FIGS. 1B and 1C are perspective views of a pelvic implant.
Figure 1C:
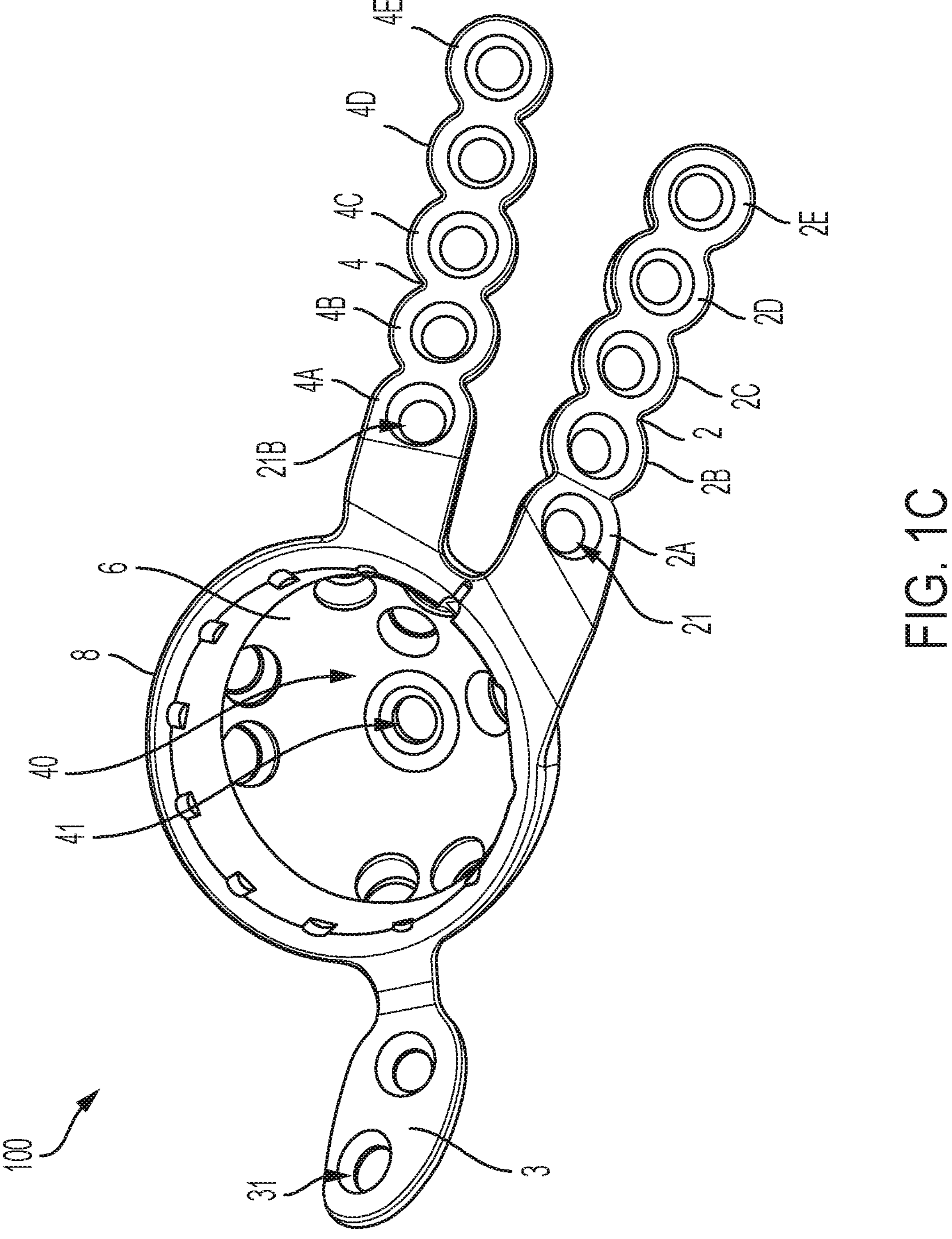

Reference is now made to FIGS. 1B and 1C, which are perspective views of an implant 100 of the present disclosure. The fastening brackets 2 and 4, and the caudal flange 3 are arranged protruding radially outward on the fastening ring 8. In this embodiment of FIGS. 1B and 1C, the fastening brackets 2 and 4, the caudal flange 3 and the fastening ring 8 are made of a single, unitary piece of material, however, in other embodiments the fastening brackets 2 and 4, the caudal flange 3 and the fastening ring 8 are two or more pieces joined together in any suitable way.

The implant 100, including the fastening brackets 2 and 4, the caudal flange 3 and the fastening ring 8, can be formed of any suitable same or different material, such as a biocompatible material, metal(s), ceramic(s), carbon based material(s), plastic(s), etc., and combinations thereof. As used herein, the term "biocompatible" or "biocompatible material" refers to any material which upon implantation into a mammal's body that does not elicit a substantial detrimental response in vivo, and/or a material exhibiting essentially no cytotoxicity or immunogenicity while in contact with body fluids, tissues and/or bones. For example, the biocompatible material can be selected from the group consisting of titanium (of any grade), Nitinol®, steel, surgical steel, calcium, copper, zinc, iron, cobalt, magnesium, manganese, vanadium, molybdenum, silicate, strontium, tungsten, chromium, nickel, aluminum, and ceramics, composites, alloys (such as TiAl6V4), compounds, and mixtures thereof.

In FIGS. 1B and 1C, the fastening ring 8 delimits an inner region 40 which is designed to receive a socket 6. In this embodiment, the fastening ring 8 extends fully circumferentially, although this is not necessary, the fastening ring 8 does not need to be completely closed and in other embodiments the fastening ring 8 can be partially open.

In FIGS. 1B and 1C, the fastening brackets 2 and 4, the caudal flange 3 and the fastening ring 8 can be made of a material that is capable of being deformed manually into a configuration shown in FIG. 1A. It is therefore possible for the operator to at least partially reshape the fastening brackets 2 and 4, the caudal flange 3 and the fastening ring 8 even during the implantation, i.e., during the operation, if necessary, and thus better adapt them to the particular anatomical features of the pelvic bone 9 of the respective patient.

As seen in FIG. 1C, the fastening bracket 2 includes five links, links 2A-2E, with the fastening bracket 4 also including five links, links 4A-4E. Each of fastening brackets 2 and 4 include five links in this embodiment, however, in other embodiments, fastening brackets 2 and 4 can include the same or different numbers of links as compared to each other, and can include one link, two links, three links, four links, six links or more links, each of the same or varying sizes. Each of the links of the fastening brackets 2 and 4 includes a circular link opening, 21A and 21B, respectively, however, in other embodiments any or all of link openings 21A and 21B can be solid such that no opening is present. The caudal flange 3 is a singular link, but in other embodiments, the caudal flange 3 can include two or more links.

Although the fastening brackets 2 and 4, the caudal flange 3 and the fastening ring 8 can be made of a material that is capable of being deformed manually, portions, or entireties, of the fastening brackets 2 and 4, and the caudal flange 3 cannot by just manual deformation, a separate tool is needed.

Figure 2:
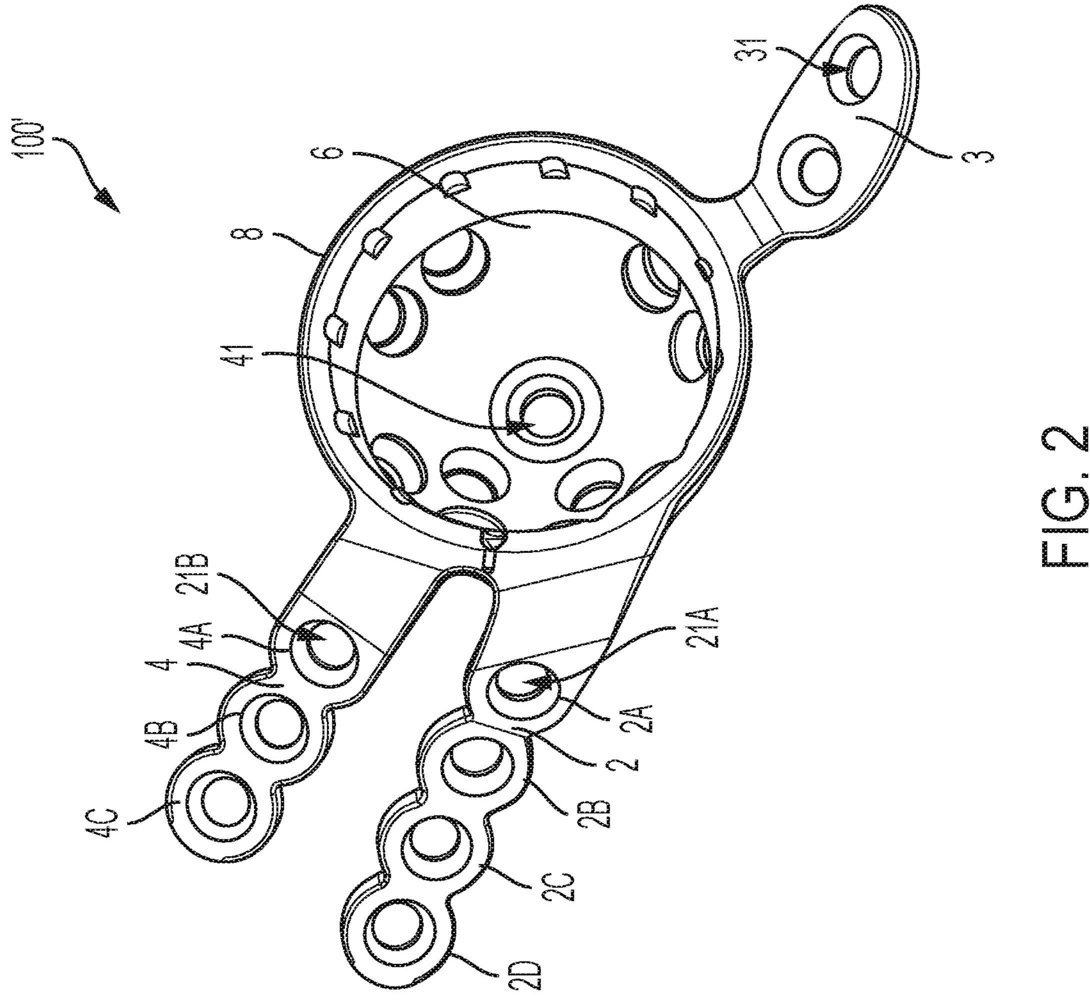
FIG. 2 is a perspective view of a pelvic implant.
Figure 3:
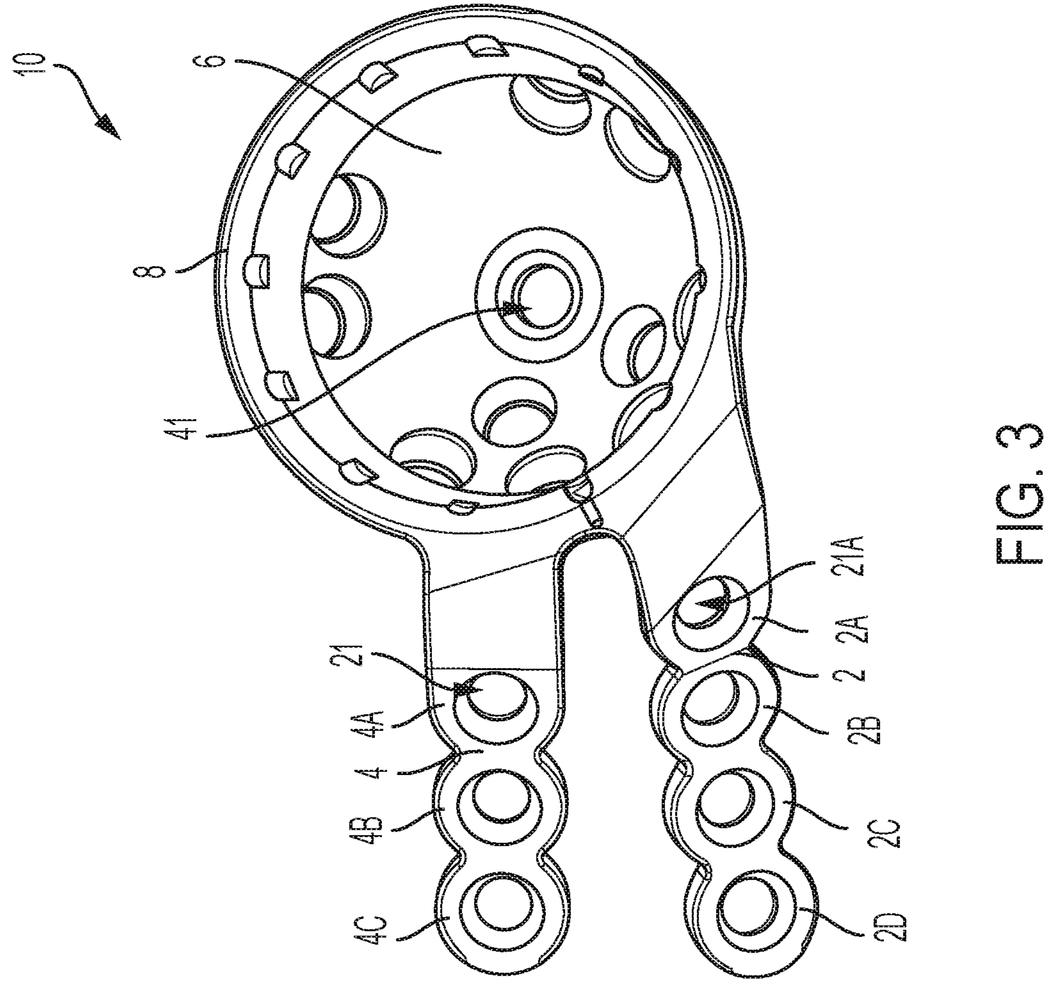
FIG. 3 is a perspective view of a pelvic implant.

A separate tool can be used to remove one or more portions from any or all of the fastening brackets 2 and 4, and the caudal flange 3, so that the implant 100 is changed from the version represented in FIGS. 1B and 1C, to a version such as the ones shown in FIGS. 2 and 3.

In FIG. 2, links have been removed from each of the fastening bracket 2 and the fastening bracket 4. Specifically, link 2E of fastening bracket 2 and links 4D and 4E of fastening bracket 4 have been removed. These links have been removed to form implant 100', typically at the instruction of a physician, so that implant 100' is better configured for an individual patient's anatomy prior to implantation into that patient.

In FIG. 3, links have been removed from each of the fastening bracket 2 and the fastening bracket 4. Specifically, link 2E of fastening bracket 2 and links 4D and 4E of fastening bracket 4 have been removed. In addition, the caudal flange 3 has been removed in its entirety. In other embodiments, a portion of caudal flange 3 can be removed. These links and the caudal flange 3 have been removed to form implant 100", typically at the instruction of a physician, so that implant 100" is better configured for an individual patient's anatomy prior to implantation into that patient.

Figure 4A:
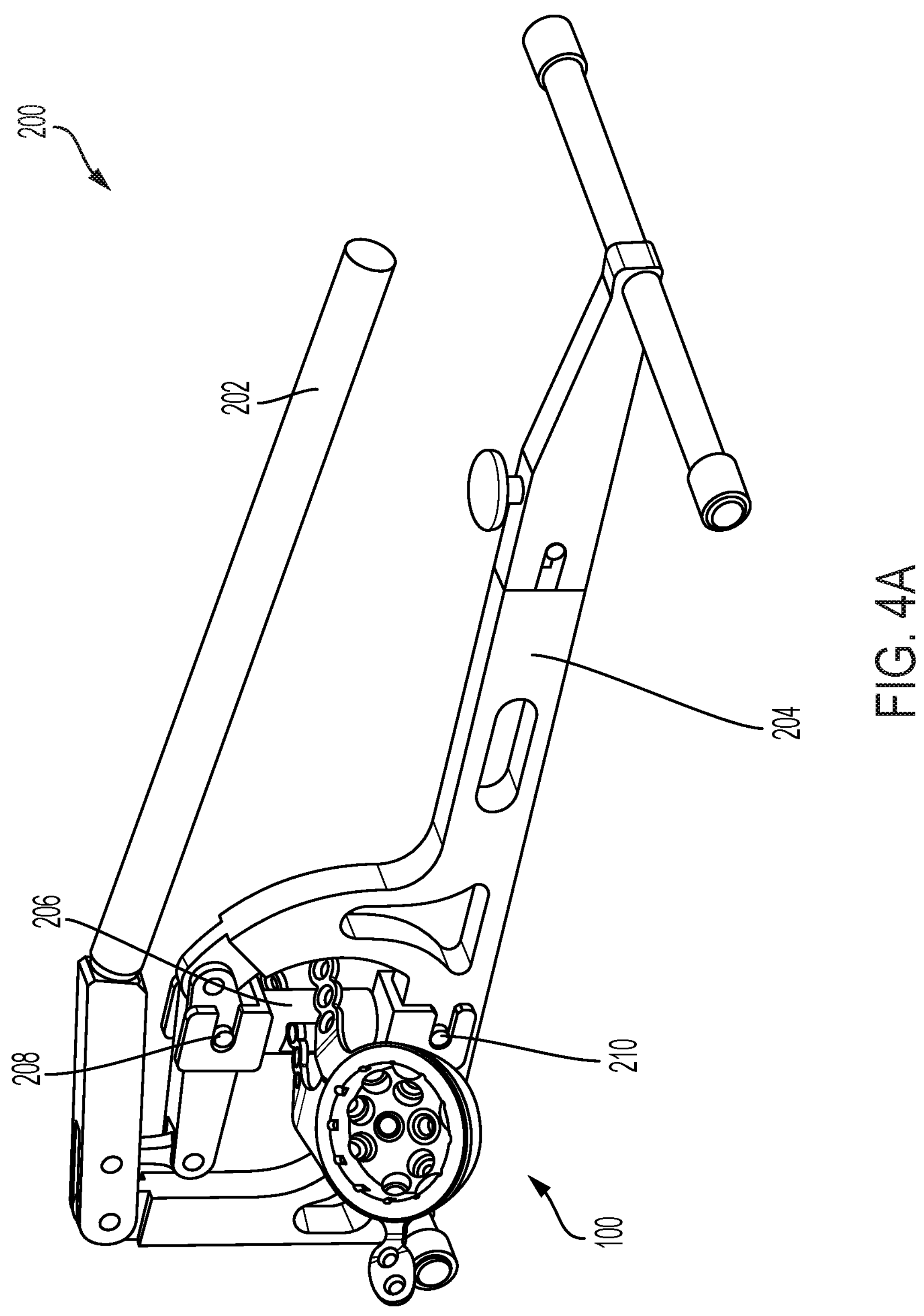
FIGS. 4A and 4B are perspective views of an assembled modification device.
Figure 4B:
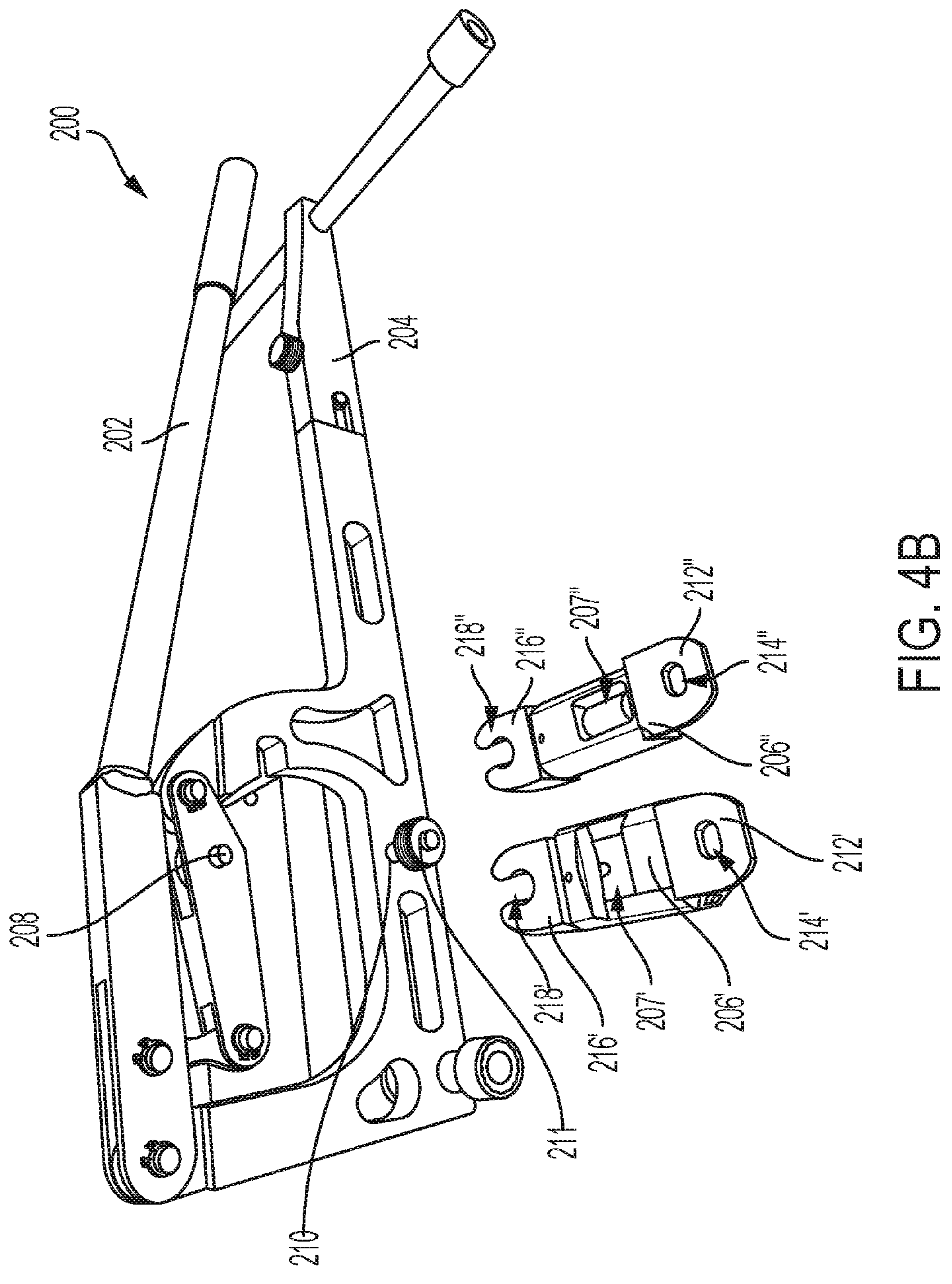

The separate tool that can be used to bend and/or remove any or all of the links and flange noted above is shown in FIG. 4A, which is a graphical representation of modification device 200, together with the implant 100 discussed above. Although FIG. 4A is illustrated together with the implant 100, in other embodiments, the modification device 200 can be used to cut any portion of any implantable structure. FIG. 4B is an image of the modification device 200.

In FIG. 4A, fastening bracket 2 is to have one or more links removed, in other embodiments any portion of any implant can be bent rather than/in addition to any portion of any implant being removed. The modification device 200 includes a handle 202 and a base 204. Handle 202 and base 204 are shown in this figure in one shape and size, but in other embodiments, handle 202 can be any shape/size/orientation so long as it can transfer an energy and/or force to a modification tool 206, and base 204 can be any shape/size/orientation so long as it can substantially support other elements of the modification device 200 relative to a supporting surface the base 204 at least partially rests on, such as a table and/or floor.

The handle 202 is configured to move up and down (further from base 204 and nearer to base 204) upon reception of a movement force, either manually or by a reception of power from a motor, etc. The handle 202 can be connected to the modification device 200 in any suitable way, such as a screw and/or bolt configuration, a snap fit configuration, a cotter pin configuration, etc. The suitable connection between the handle 202 and the rest of the modification device 200 can be such that the handle 202 is removable and its removal can be effected manually, without the use of tools.

The movement of the handle 202 provides a modification force to, and causes movement of, modification tool 206. This modification force, received by the modification tool 206, is configured to provide a modification force to a portion of the implant, the modification force being a bending force and/or a cutting/separating force.

The force received by the handle 202 and the modification force can be the same or different depending on the force added or subtracted by the geometry of the handle 202 and the optional components between the handle 202 and the modification tool 206. In this embodiment, the modification tool 206 is configured to remove a portion of the implant. This removal of a portion of the implant is by a separation and/or cutting procedure, where a portion(s) of the material of the implant is separated from another portion(s) of the implant. The modification tool 206 is shown in more detail in later figures.

An upper support 208 and a lower support 210 are configured to maintain the modification tool 206 in a position, between the handle 202 and the base 204, so that the modification tool 206 can receive a force and/or energy from the handle 202.

In FIG. 4B, two different embodiments of modification tools are shown, modification tool 206' and 206". Modification tool 206' is configured to cut relatively wider portions of material, such as caudal flange 3. Modification tool 206" is configured to cut relatively narrower portions of material, such as fastening bracket 2.

To maintain modification tool 206' in the modification device 200, modification device upper portion 212' is moved so that upper support 208 extends through modification device upper opening 214', and modification device lower portion 216' is moved so that lower support 210 extends through a portion of modification device lower slot 218'. After the lower support 210 is moved to extend through a portion of the modification device lower slot 218', securing device 211 is placed onto the lower support 210 to contact the modification device lower portion 216', substantially maintaining the modification tool 206' shown in FIG. 5B. The securing device 211 can be any structure that is configured to maintain the modification device lower portion 216' in a position relative to the rest of the modification device 200, such as a screw and/or bolt configuration, a snap fit configuration, a cotter pin configuration, etc.

Similarly, to maintain modification tool 206" in the modification device 200, modification device upper portion 212" is moved so that upper support 208 extends through modification device upper opening 214", and modification device lower portion 216" is moved so that lower support 210 extends through a portion of modification device lower slot 218". After the lower support 210 is moved to extend through a portion of the modification device lower slot 218", securing device 211 is placed onto the lower support 210 to contact the modification device lower portion 216", substantially maintaining the modification tool 206" shown in FIG. 5B. The securing device 211 can be any structure that is configured to maintain the modification device lower portion 216" in a position relative to the rest of the modification device 200, such as a screw and/or bolt configuration, a snap fit configuration, a cotter pin configuration, etc.

Examples of the connection of the modification tool 206" to the modification device 200 are described above, and also include any other suitable connection. The connection between the modification tool 206" and the rest of the modification device 200 can be such that the modification tool 206" is removable and its removal can be effected manually, without the use of tools.

Figure 5A:
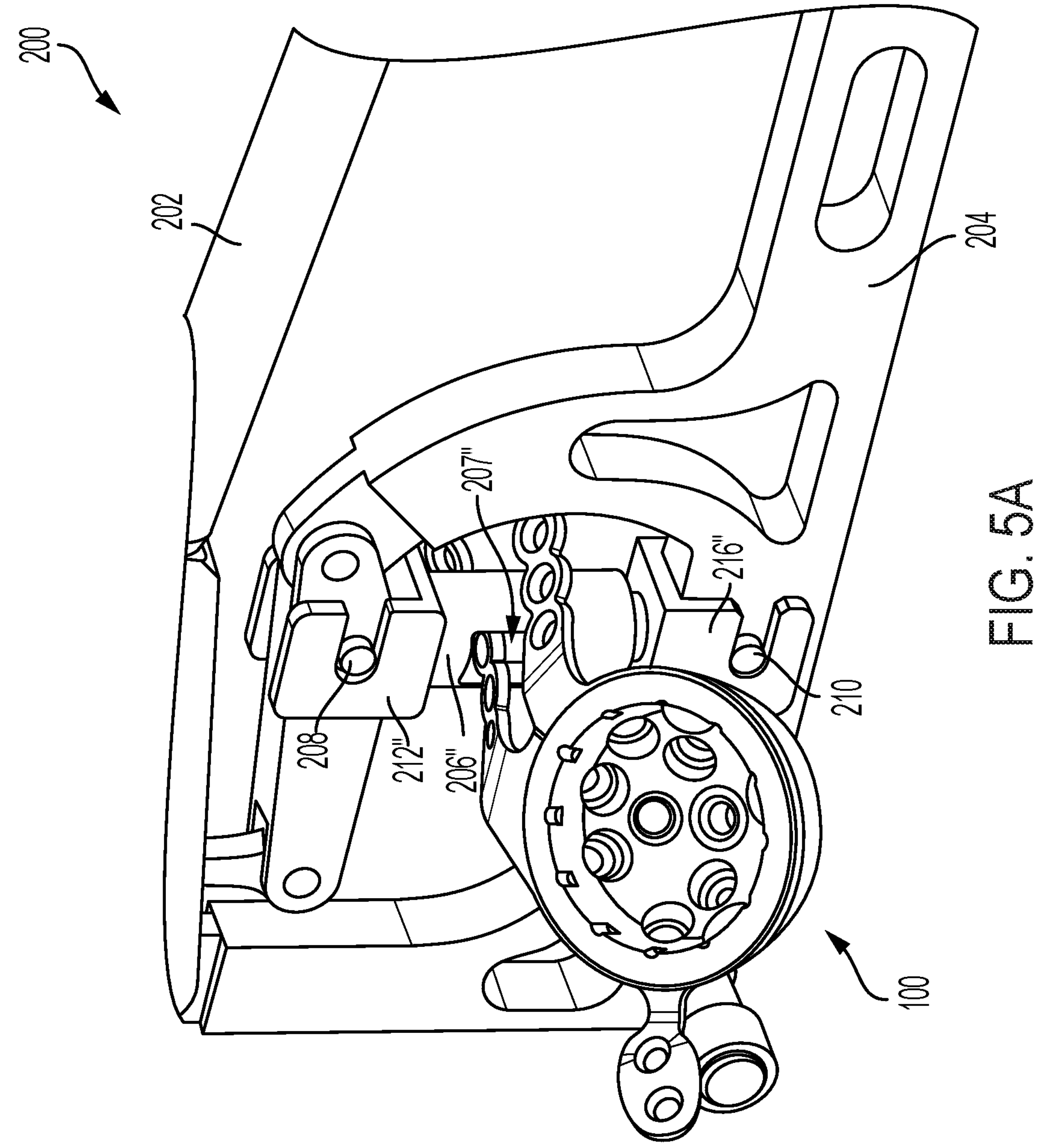
FIG. 5A is a perspective view of a modification device and a tab of a pelvic implant.

FIG. 5A is a magnified view of modification tool 206" with a portion of the implant 100 extending through a modification opening 207" of the modification tool 206". This modification opening 207" is dimensioned to receive and cut a portion of the fastening bracket 2 of the implant 100. For example, during a cutting operation of the modification device 200, the handle 202 can be moved, the modification opening 207" can close and link 2E (as seen in FIG. 1C) can be cut off of the fastening bracket 2 (as seen in FIG. 2). In the embodiment of FIG. 5A, the modification device upper portion 212" and modification device lower portion 216" are differently shaped as compared to those in FIG. 4B, thus, any suitable size and shape of these features can be included in the modification device 200. The configuration of the modification tool 206" in FIG. 5A is an open configuration, such that modification opening 207" is in an open configuration and portion(s) of the implant 100 can be passed therethrough and can be cut.

Figure 5B:
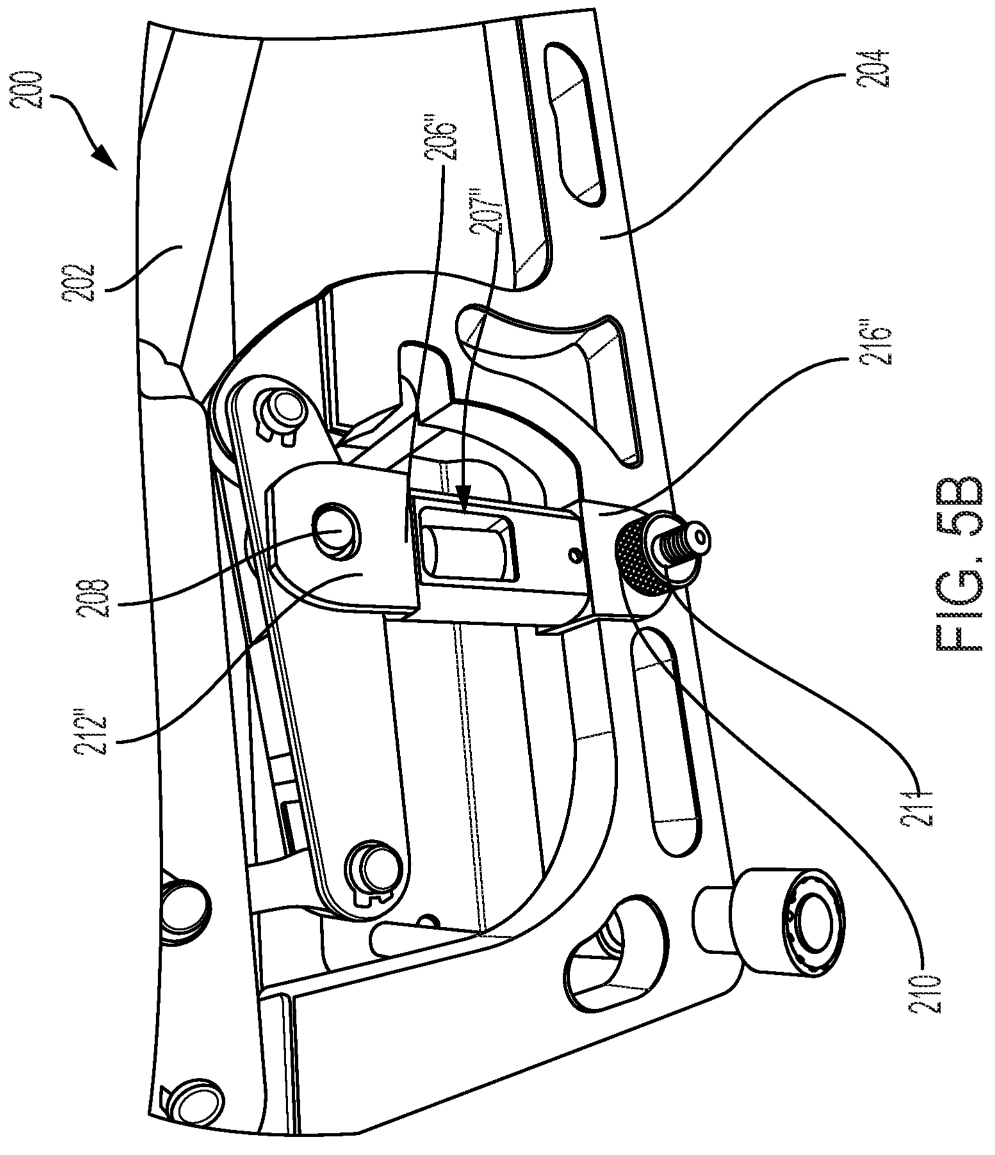
FIG. 5B is a magnified, perspective view of the cutting slot of the modification tool.

FIG. 5B is an image of modification tool 206", similar to the illustration of FIG. 5A, without implant 100 being included. The configuration of the modification tool 206" in FIG. 5B is a closed configuration, such that modification opening 207" is in a closed configuration.

Figure 5C:
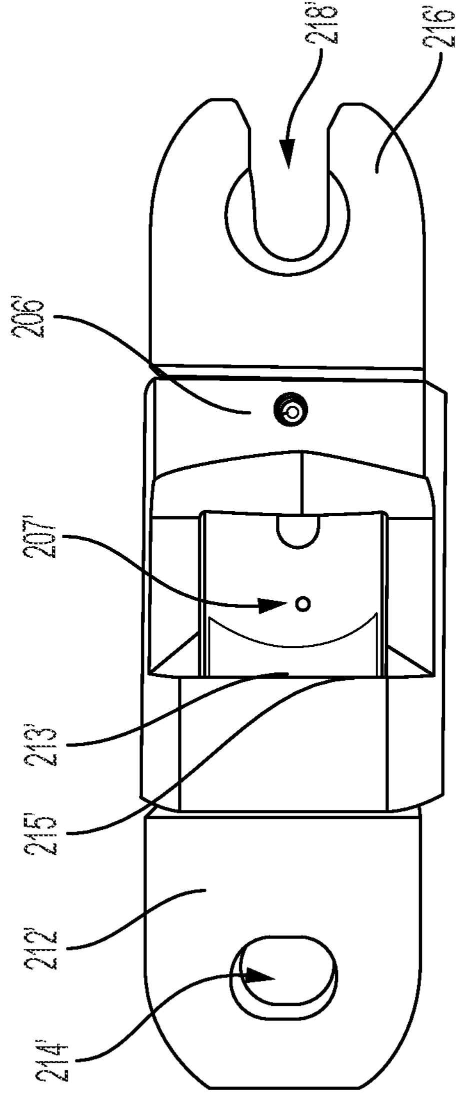
FIG. 5C is a magnified, top view of modification tools.
Figure 5C:
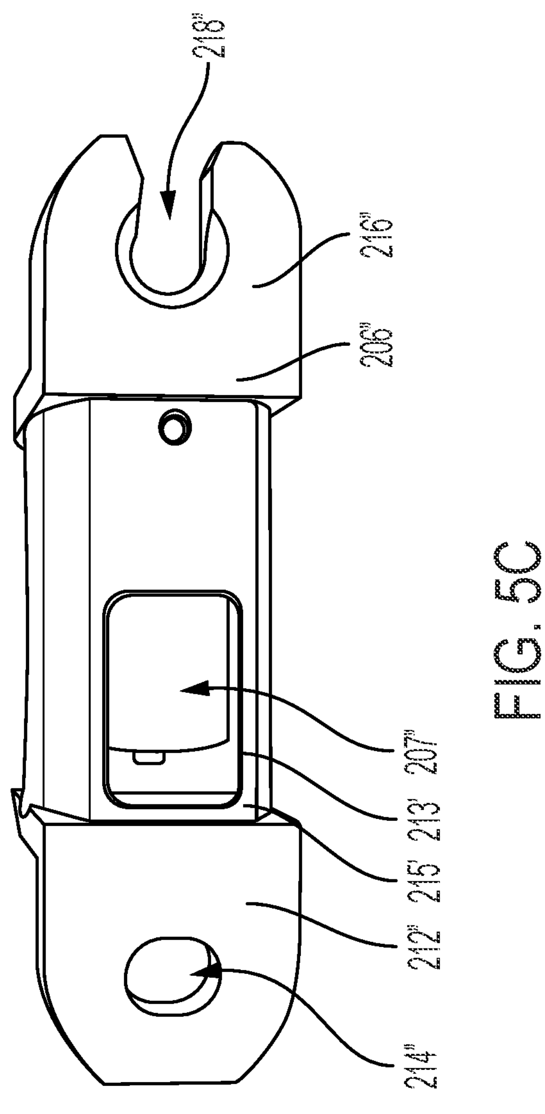

FIG. 5C is a magnified view of a rear face of each of modification tool 206' and modification tool 206", each in an uninstalled configuration. The rear face of each of modification tool 206' and modification tool 206" is configured to face towards and/or contact or nearly contact the modification device 200 when the modification tool 206' and modification tool 206" are in the installed configuration. Each of modification tool 206' and modification tool 206" are in a closed configuration, such that their respective modification openings 207' and 207" are closed or substantially closed, such that a portion of an implant cannot be passed therethrough.

In an open configuration of each of modification tool 206' and modification tool 206", a portion of an implant can pass through their respective modification openings 207' and 207", between a movable cutter surface 213'/213" and a fixed surface 215'/215". Upon moving the handle 202, the movable cutter surface 213'/213" receives a movement power, and moves nearer and further from the fixed surface 215'/215". To perform a cutting/separating process, the portion of the implant to be cut is placed in the modification opening 207'/207", the handle 202 is moved to provide a modification force to the implant, the movable cutter surface 213'/213" moves towards the fixed surface 215'/215", cutting the portion of the implant therebetween. The cut portion of the implant can be in any suitable shape based on the shape of the movable cutter surface 213'/213" and the fixed surface 215'/215", which can be interchanged independently, as desired.

Figure 6:
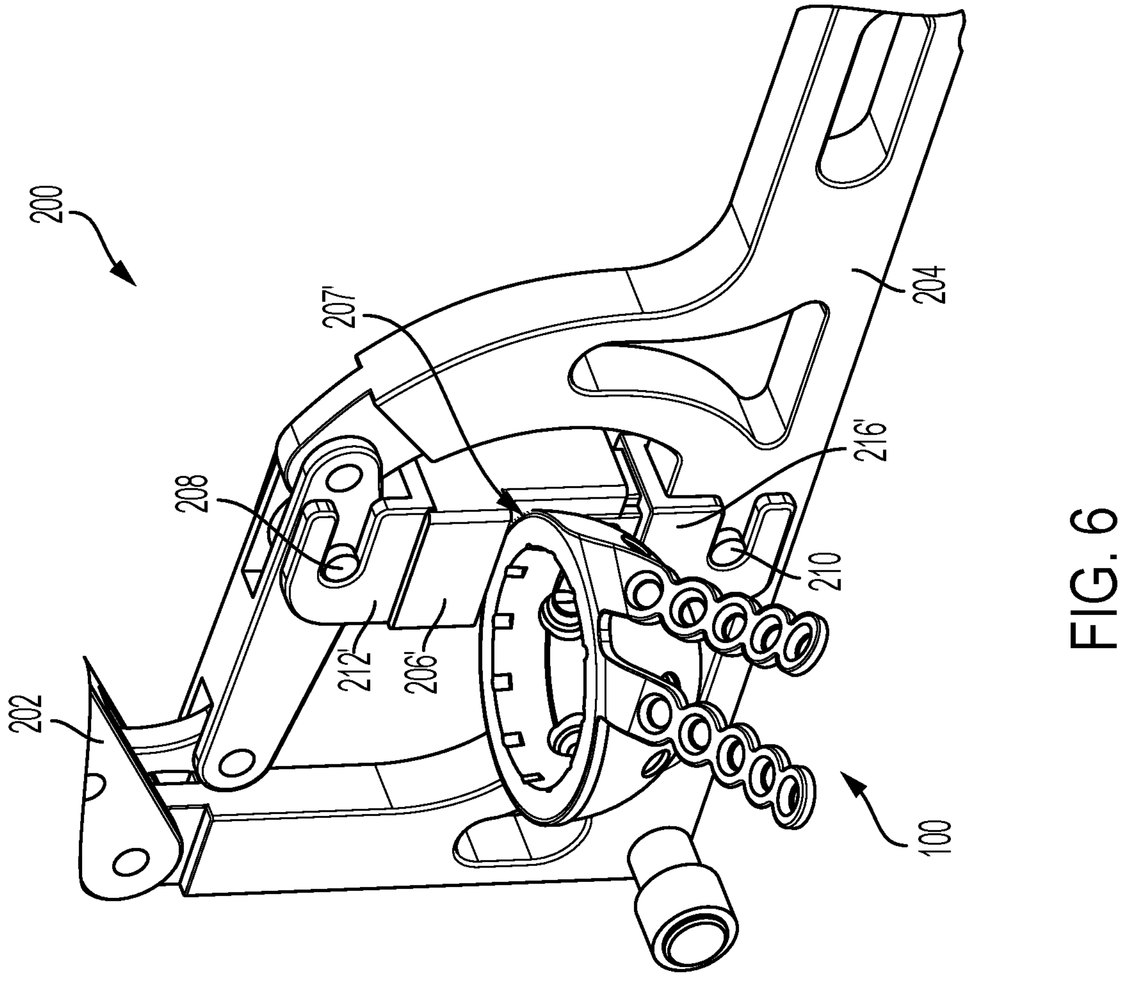
FIG. 6 is a perspective view of a modification device and a caudal flange of a pelvic implant.

FIG. 6 is a magnified view of modification tool 206' with a portion of the implant 100 extending through a modification opening 207" of the modification tool 206'. This modification opening 207' is dimensioned to receive and cut a portion of the caudal flange 3 of the implant 100. For example, during a cutting operation of the modification device 200, the handle 202 can be moved, the modification opening 207' can close and caudal flange 3 (as seen in FIG. 1C) can be cut off of fastening ring 8 (as seen in FIG. 3). In the embodiment of FIG. 6, an entire caudal flange 3 can be removed so that the fastening ring 8 can be substantially curved about its perimeter, in other embodiments, one or more portions of the caudal flange 3 (or any other portion of implant 100) can be removed by modification tool 206'.

In the embodiment of FIG. 6, the modification device upper portion 212' and modification device lower portion 216' are differently shaped as compared to those in FIG. 4B, thus, any suitable size and shape of these features can be included in the modification device 200. The configuration of the modification tool 206' in FIG. 6 is an open configuration, such that modification opening 207' is in an open configuration and portion(s) of the implant 100 can be passed therethrough and can be cut.

Figure 7A:
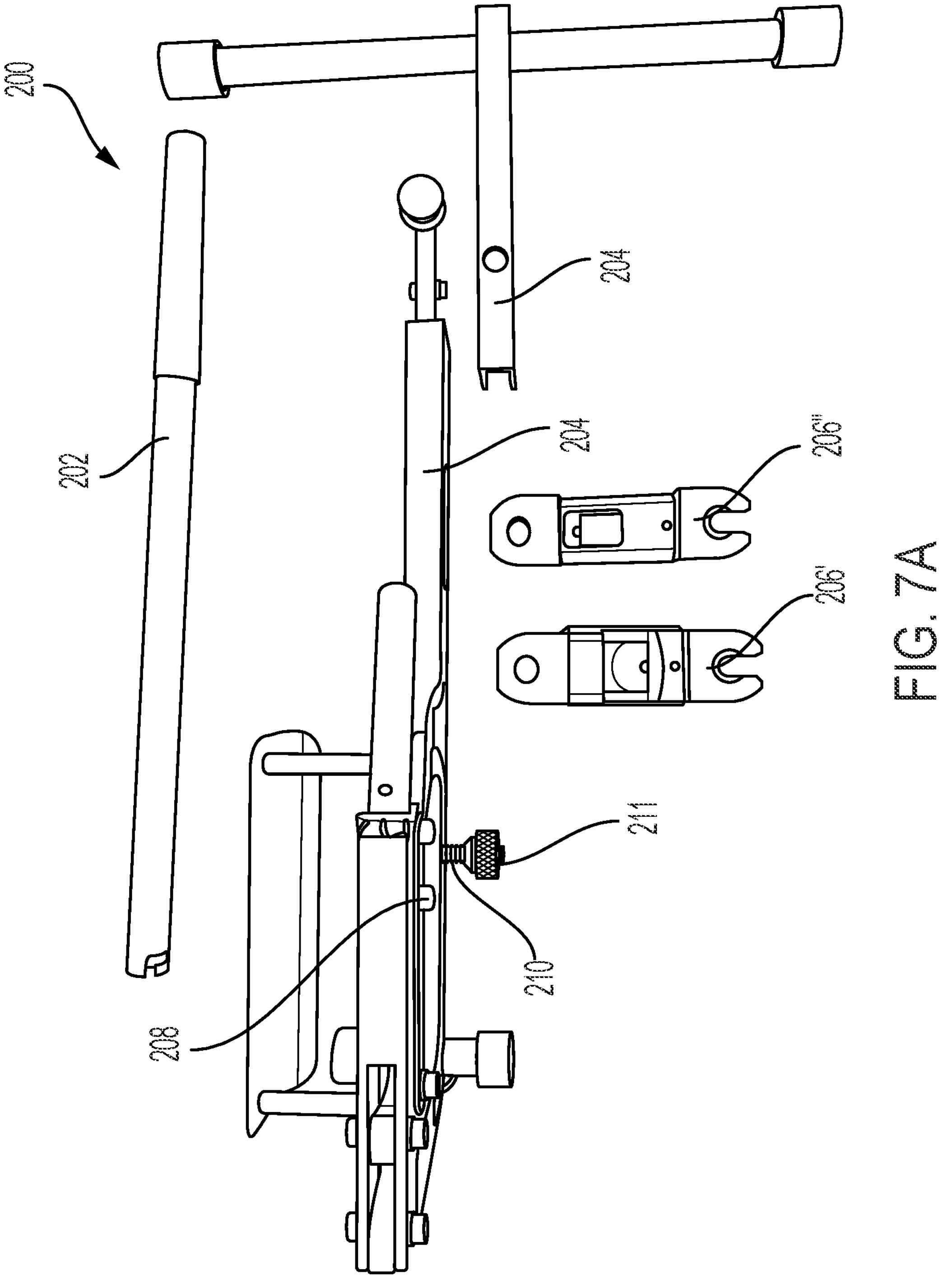
FIG. 7A is a top view of a disassembled implant modification device.

FIG. 7A is an image of the modification device 200 in a disassembled configuration. To change the modification device 200 into the disassembled configuration from the assembled configuration (shown in FIG. 4A), the modification device 200 can undergo a disassembly method, which can proceed according to any suitable order of steps.

Modification tool 206' and modification tool 206" are removed from between the handle 202 and the base 204 of the modification device 200. The handle is removed from the rest of the modification device 200. The base 204 can be separated into two pieces, base 204A and base 204B. Then the modification tool 206, the handle 202, the base 204A and the base 204B can all be placed into a sterilization basket 220, shown in FIG. 7B and discussed below.

Removal of these components can be relatively easily accomplished, by manual operation and/or use of a tool, with the structure of the modification device changed to the configuration shown in FIG. 7A through a removal/disconnection process. For example, the separated components of FIG. 7A are held in an assembled configuration by structure(s) that are configured to maintain the elements relative to the other portion(s) of the modification device 200 such as a screw and/or bolt configuration, a snap fit configuration, a cotter pin configuration, etc. Thus, to change the modification device 200 into the disassembled configuration of FIG. 7A, the components can be removed without the use of tools.

Figure 7B:
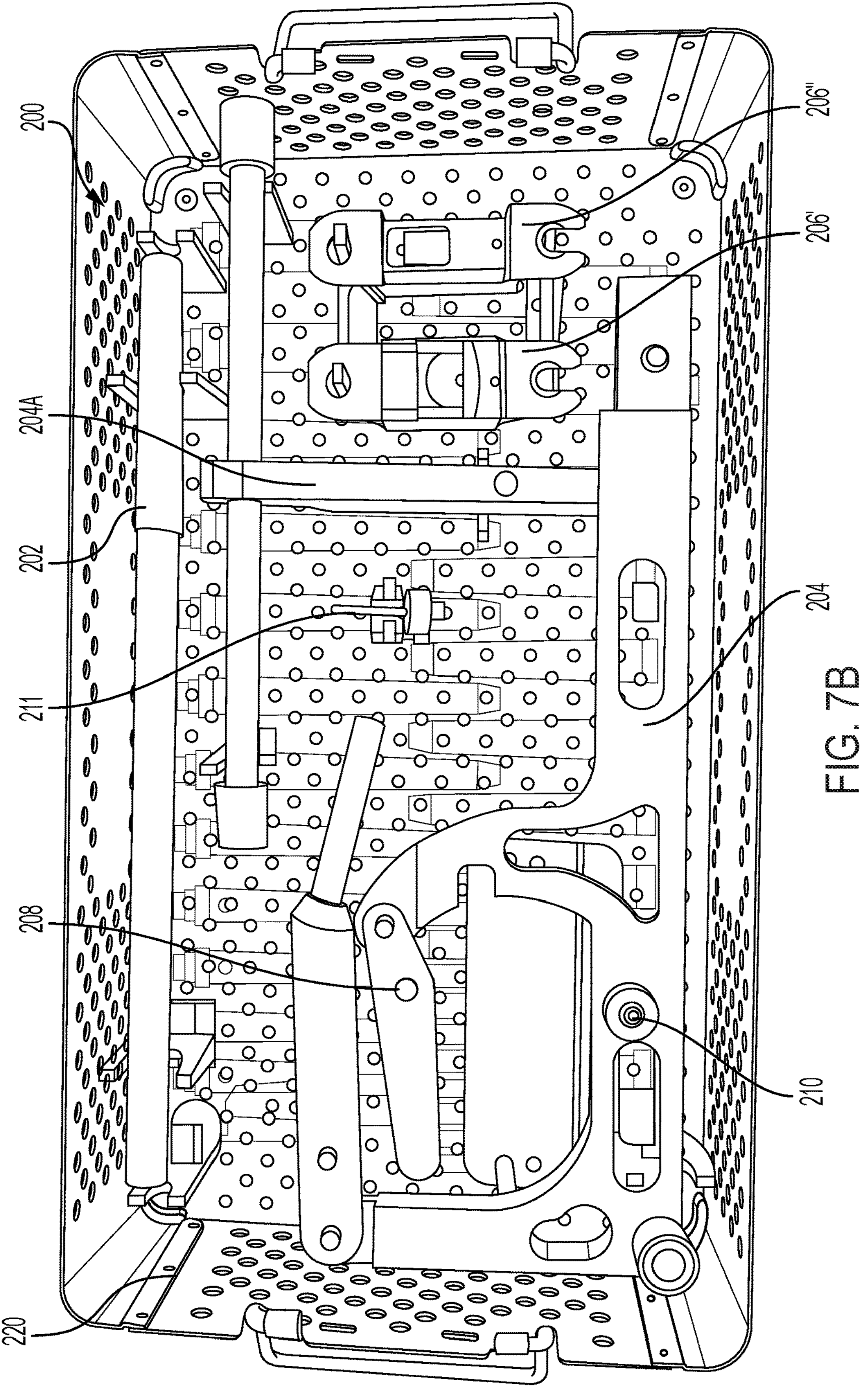
FIG. 7B is a top view of a disassembled implant modification device placed within a sterilization basket.

Such a disassembled configuration, achieved without the use of tools, as shown in FIG. 7A, can make transport of the modification device 200 more efficient due to a smaller overall footprint, and can make cleaning of the modification device 200 easier, such as by placing the disassembled components into the sterilization basket 220, as shown in FIG. 7B.

The sterilization basket 220 can be any suitable size and shape to fit within it at least a portion of the components of the modification device 200. In the embodiment of FIG. 7B, the sterilization basket 220 is dimensioned so that all components of the disassembled modification device 200 can fit within the sterilization basket 220 with little or no contact between the components. In the assembled configuration of FIG. 4A, the overall volume (the polygon of space created by the furthest exterior points of the modification device 200) and the footprint on any supporting surface of the modification device 200 is larger than the volume of the sterilization basket 220 of FIG. 7B and/or larger than the footprint of the sterilization basket 220 of FIG. 7B. Thus, the disassembled configuration of the modification device 200, within the sterilization basket 220

Thus, to clean the components of the modification device 200, the sterilization basket 220 and components therein, as seen in FIG. 7B, can all be placed within a sterilization chamber (not shown) and expose the components of the modification device 200 and the sterilization basket 220 to a sterilizing procedure, and upon completion of a sterilizing procedure, can all be removed by handling of the sterilization basket 220. As used herein, the term "sterilize(d)" or "sterilization" or "sterilizing" means a reduction in the level of at least one active biological contaminant or pathogen present on any surface of the modification device 200 through: exposure, for any suitable amount of time, to a liquid configured to reduce at least one active biological contaminant or pathogen on any surface of the modification device 200; and/or exposure, for any suitable amount of time, to a gas configured to reduce at least one active biological contaminant or pathogen on any surface of the modification device 200; and/or exposure, for any suitable amount of time, to a temperature environment configured to reduce at least one active biological contaminant or pathogen on any surface of the modification device 200; and/or exposure, for any suitable amount of time, to a pressure environment configured to reduce at least one active biological contaminant or pathogen on any surface of the modification device 200.

Figure 8A:
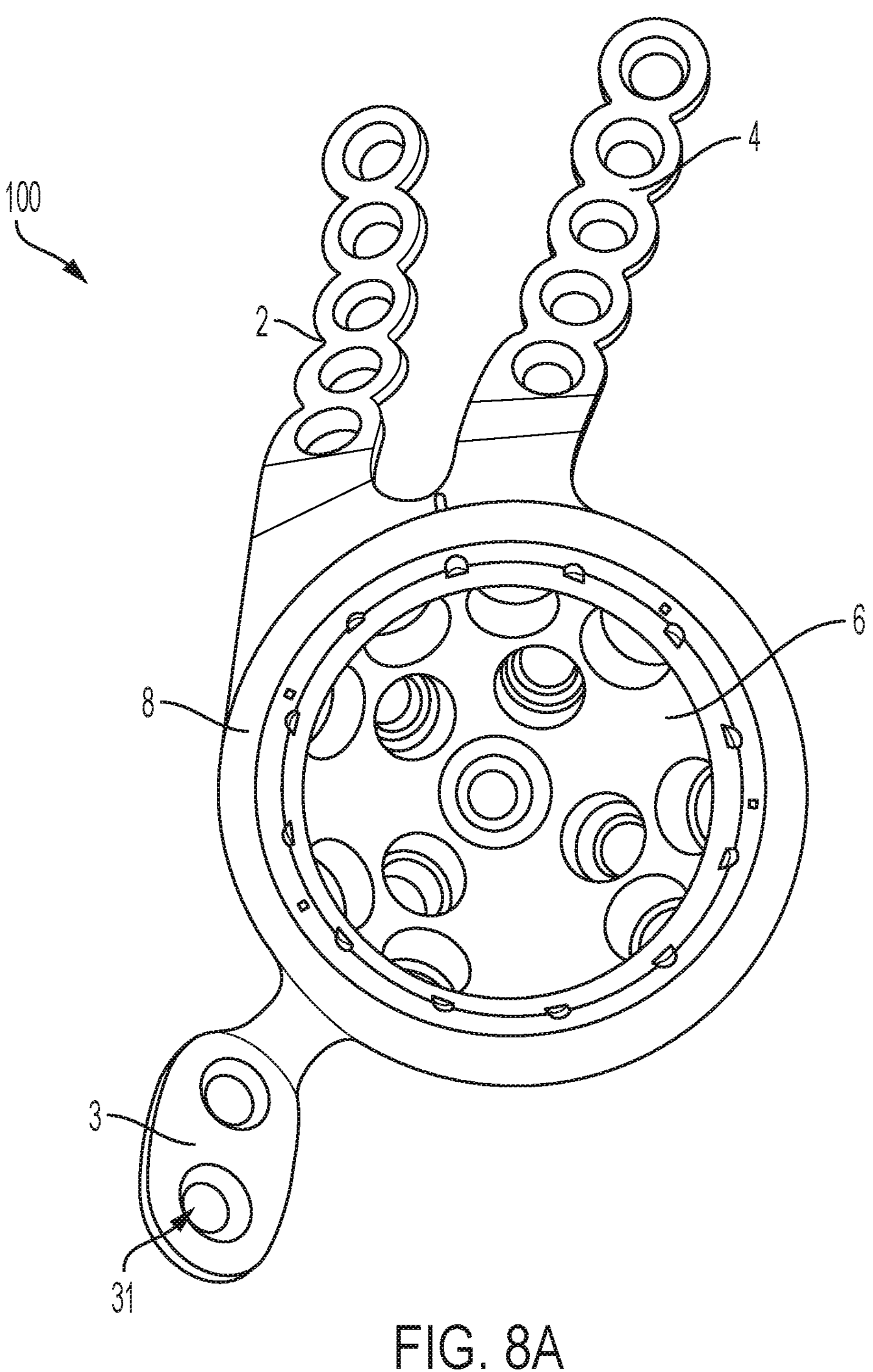
FIGS. 8A and 8B are top views of a pelvic implant.
Figure 8B:
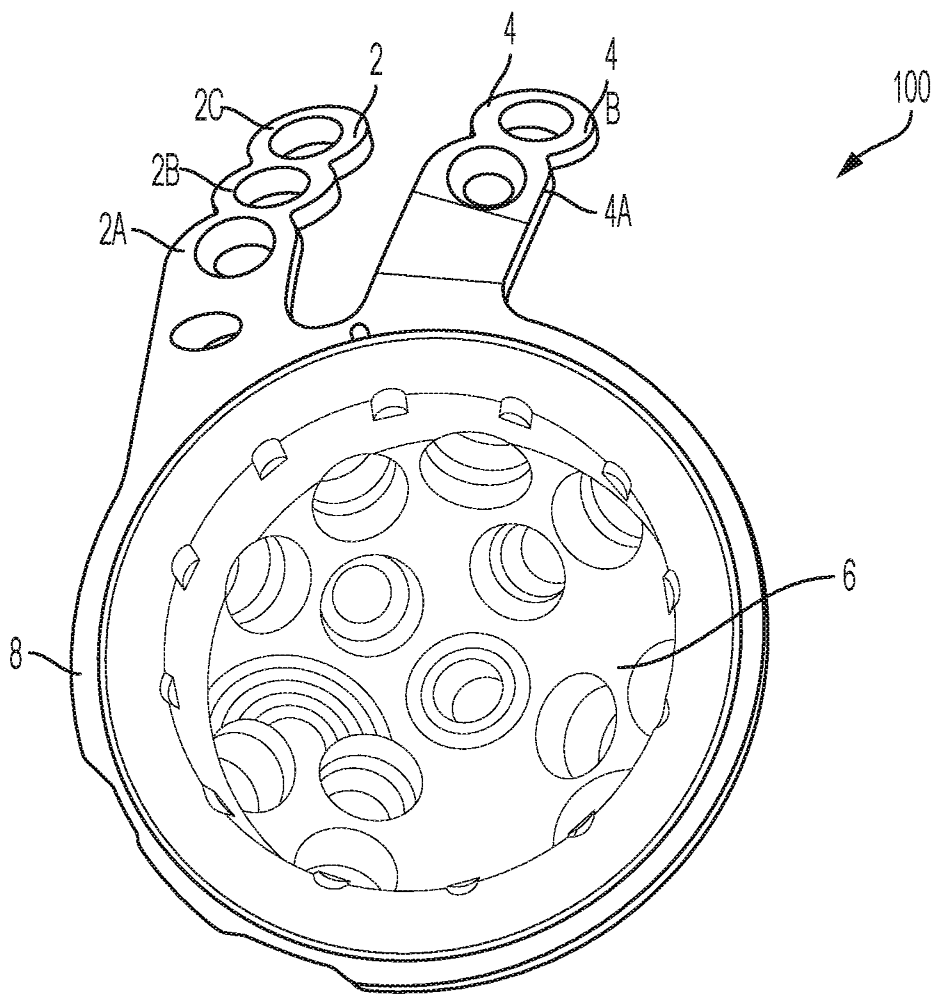

FIGS. 8A and 8B are further figures of implant 100. FIG. 8A is an image of an implant 100 that has not had any portion cut off by modification device 200. FIG. 8B is an image of an embodiment of implant 100'''. For implant 100', the caudal flange 3 has been cut off, and each of links 2D, 2E, 4C, 4D, and 4E have been cut off by modification device 200.

Figure 9A:
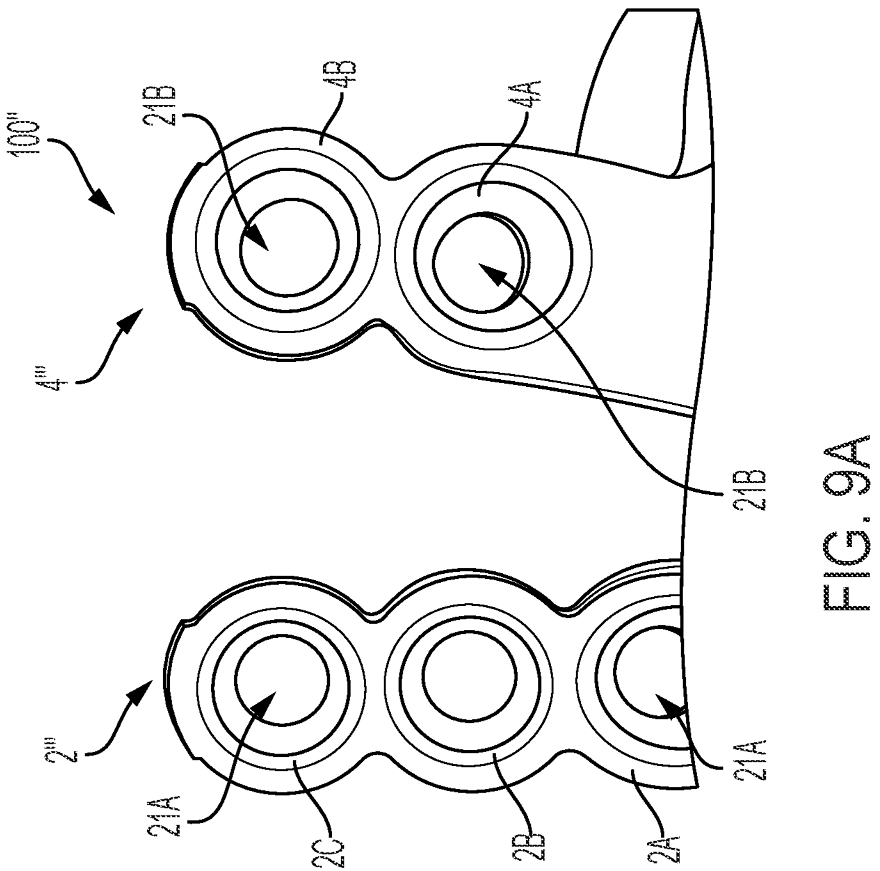
FIGS. 9A and 9B are magnified views of a pelvic implant.

A magnified portion of implant 100''' is shown in FIG. 9A, with links 2D, 2E, 4C, 4D, and 4E having been cut off by modification device 200. As can be seen in FIG. 9A, a distal end 2' and a distal end 4''' of each of fastening brackets 2 and 4 is substantially smooth, with the cut of each fastening bracket 2 and 4 substantially following the radius of curvature of openings 21A and 21B. However, in other embodiments, distal end 2''' and distal end 4''' of each of fastening brackets 2 and 4 can individually be left in any suitable shape.

Figure 9B:
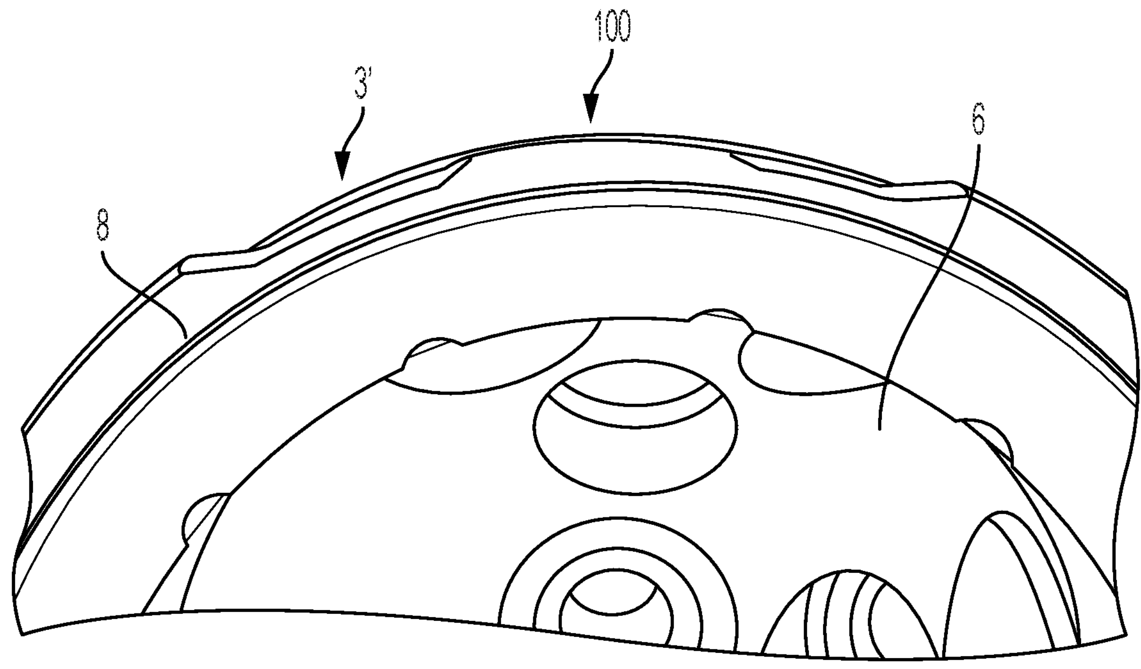

A magnified portion of implant 100''' is shown in FIG. 9B, with caudal flange 3 having been cut off by modification device 200. As can be seen in FIG. 9B, the proximal end 3' of caudal flange is substantially smooth, with the cut of the caudal flange 3 substantially following the radius of curvature of fastening ring 8. However, in other embodiments, proximal end 3' can be left in any suitable shape.

As can be seen from FIGS. 9A and 9B, the modification tool 206 can be configured so that the surface that is cut is substantially clean and substantially burr-free.

Figure 10A:
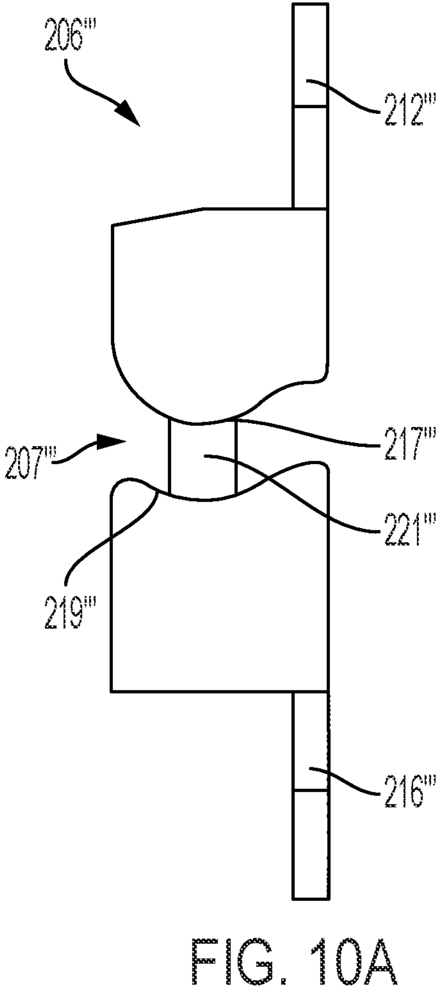
FIGS. 10A, 10B, and 10C are side, front, and perspective views, respectively, of a bending insert.

Another embodiment of a modification tool 206''' is shown, in side view, in FIG. 10A. In this embodiment, modification tool 206''' is not configured to cut a piece of material from implant 100, but is configured to bend a portion of implant 100 that is placed between an upper jaw surface 217''' and a lower jaw surface 219''', through a modification opening 207'''. In a bending procedure, the handle 202 is moved to provide a modification force to the implant so that the upper jaw surface 217''' moves closer to the lower jaw surface 219''', causing any interleaved material to bend into substantially the shape of one or both of the upper jaw surface 217''' and the lower jaw surface 219'''. In this embodiment the upper jaw surface 217''' and the lower jaw surface 219''' are curved in a complementary shape, in other embodiments, the upper jaw surface 217''' and the lower jaw surface 219''' can be any suitable shape, which can be interchanged independently, as desired, leading to an ability to customize implants.

Figure 10B:
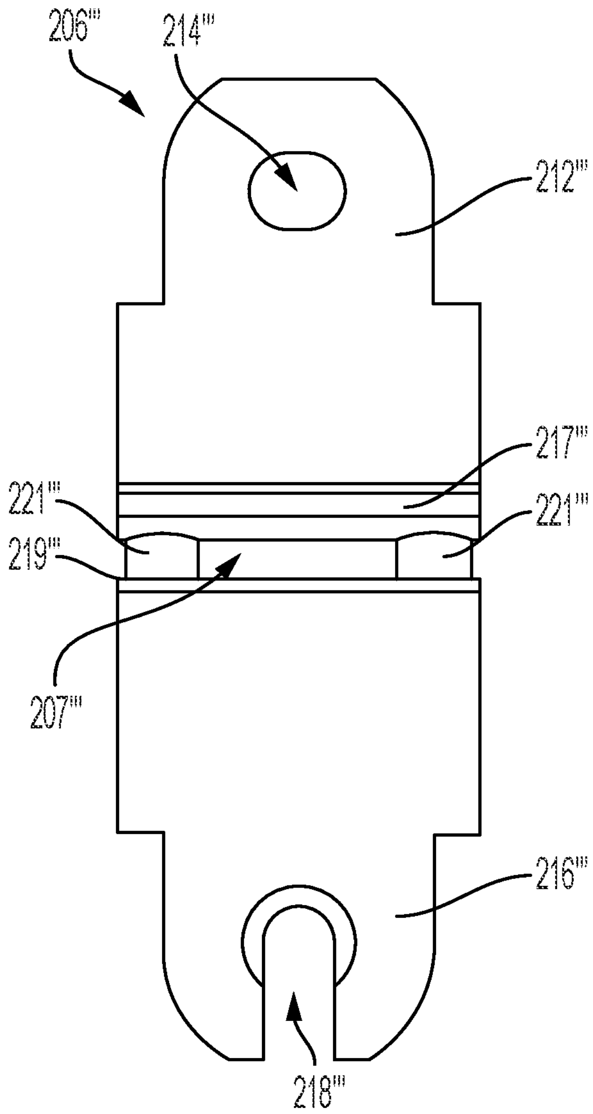
Figure 10C:
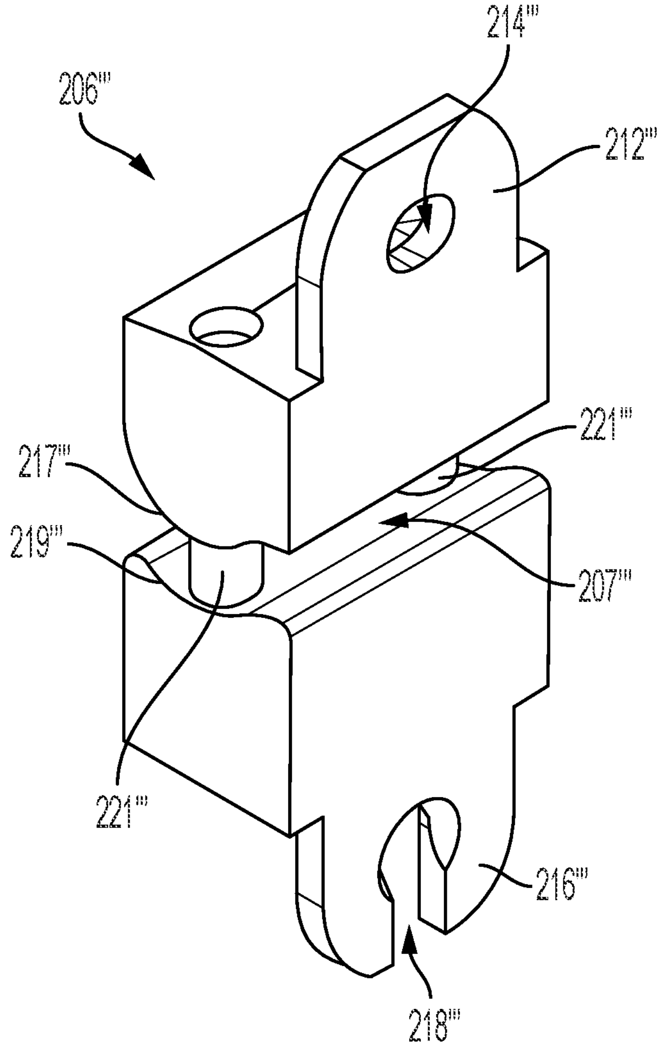

The upper jaw surface 217''' and the lower jaw surface 219''' can slide towards and away from each other along guides 221''', two of which are shown in FIG. 10A-10C, but in other embodiments, one, three or more guides can be included in modification tool 206'''.

A rear view of the modification tool 206''' is shown in FIG. 10B, and a perspective view of the modification tool 206''' is shown in FIG. 10C.

Figure 11A:
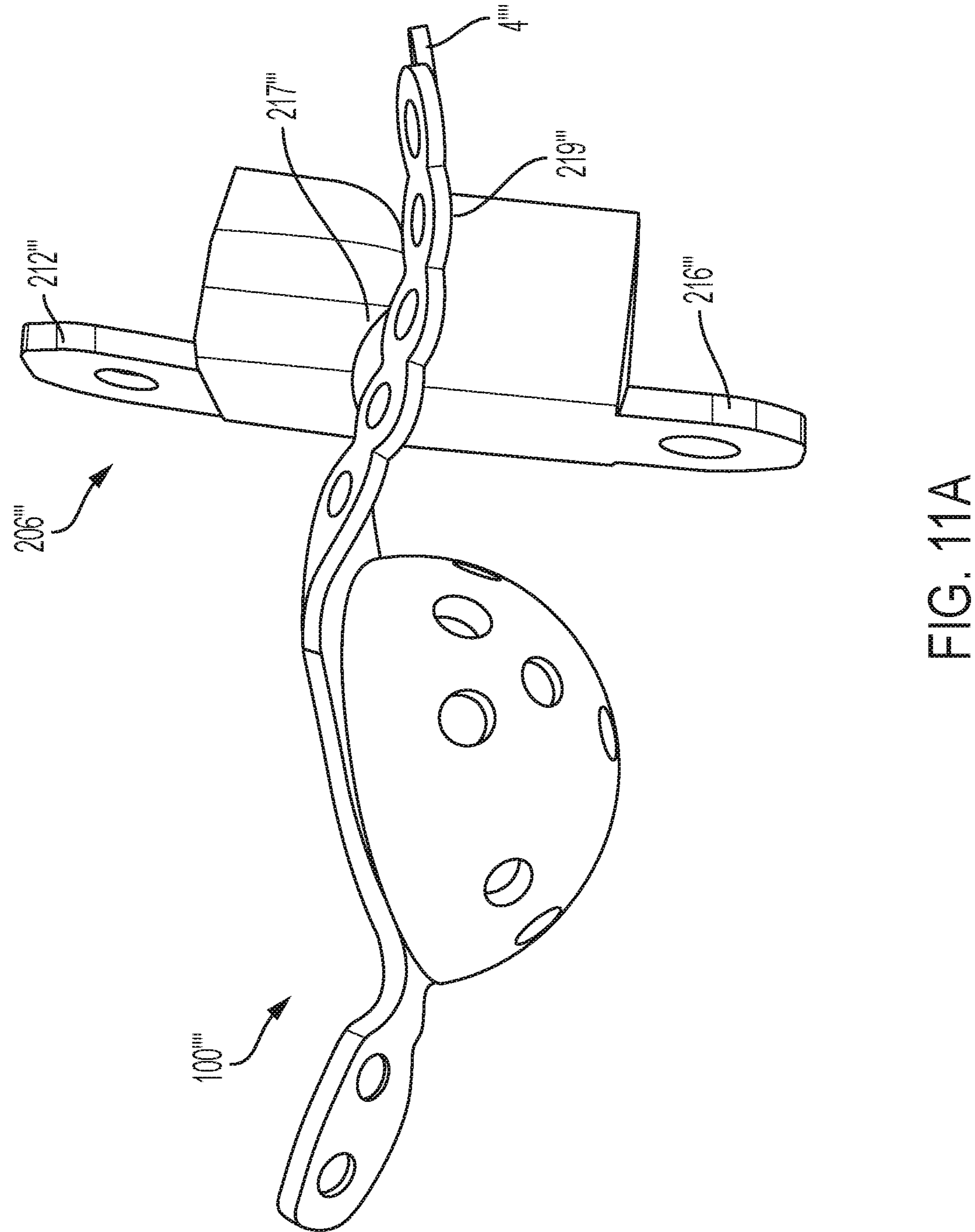
FIG. 11A is a perspective view of a tab.

FIG. 11A is an illustration of the modification tool 206''' with a portion of an implant 100'''' of a silicon or plastic material for illustrative purposes. As can be seen in FIG. 11A, a portion of a fastening bracket 4'''' is placed between the upper jaw surface 217''' and the lower jaw surface 219''', so that upon reception of a force, the upper jaw surface 217''' and the lower jaw surface 219''' can move towards each other and bend the portion of the fastening bracket 4''''.

Figure 11B:
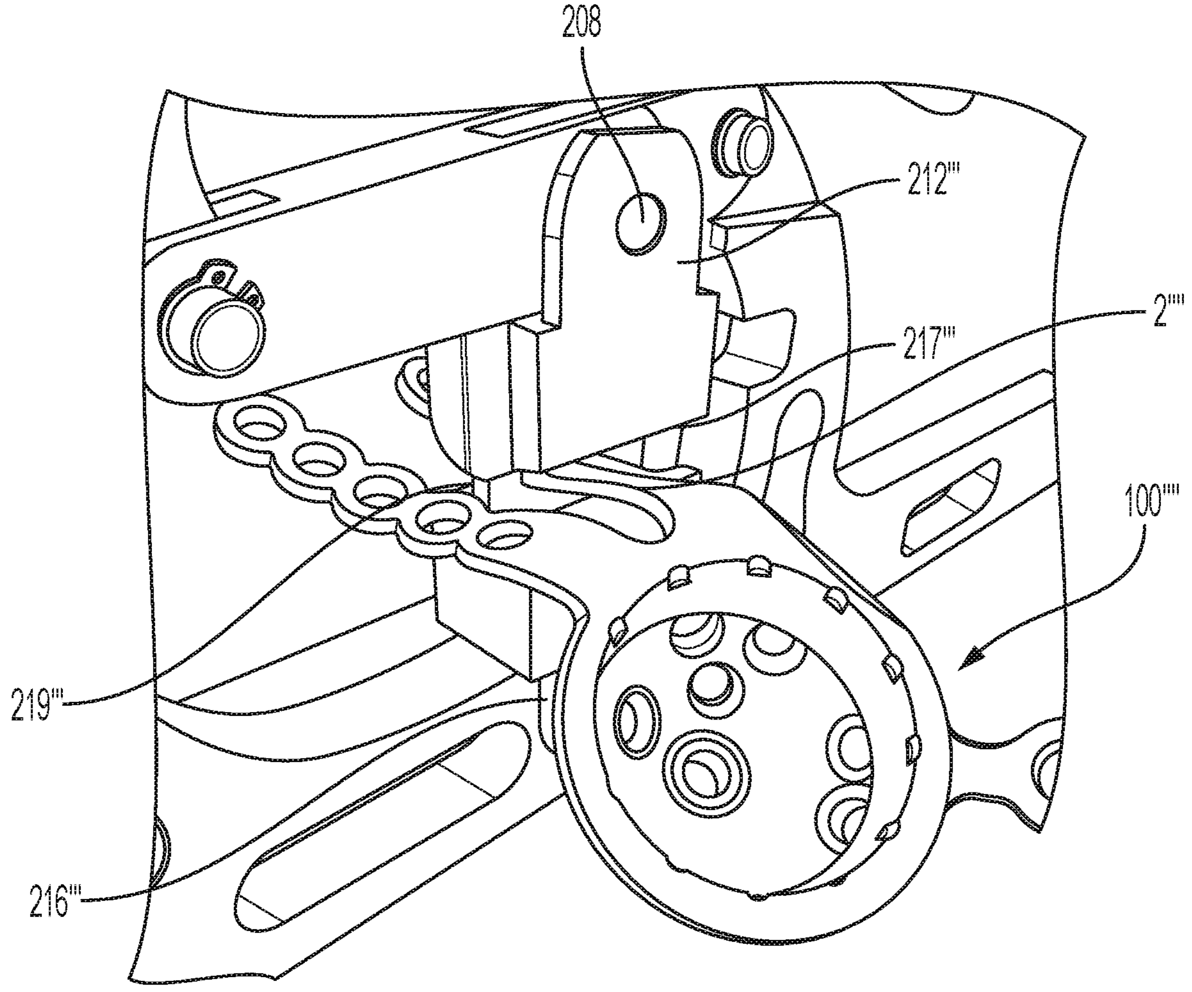
FIG. 11B is a perspective view of a tab.

FIG. 11B is an image of the modification tool 206''' with a portion of a fastening bracket 2'''' extending between the upper jaw surface 217''' and the lower jaw surface 219''', with the fastening bracket 2'''' configured to be bent by contact between the upper jaw surface 217''' and/or the lower jaw surface 219'''.

Figure 12A:
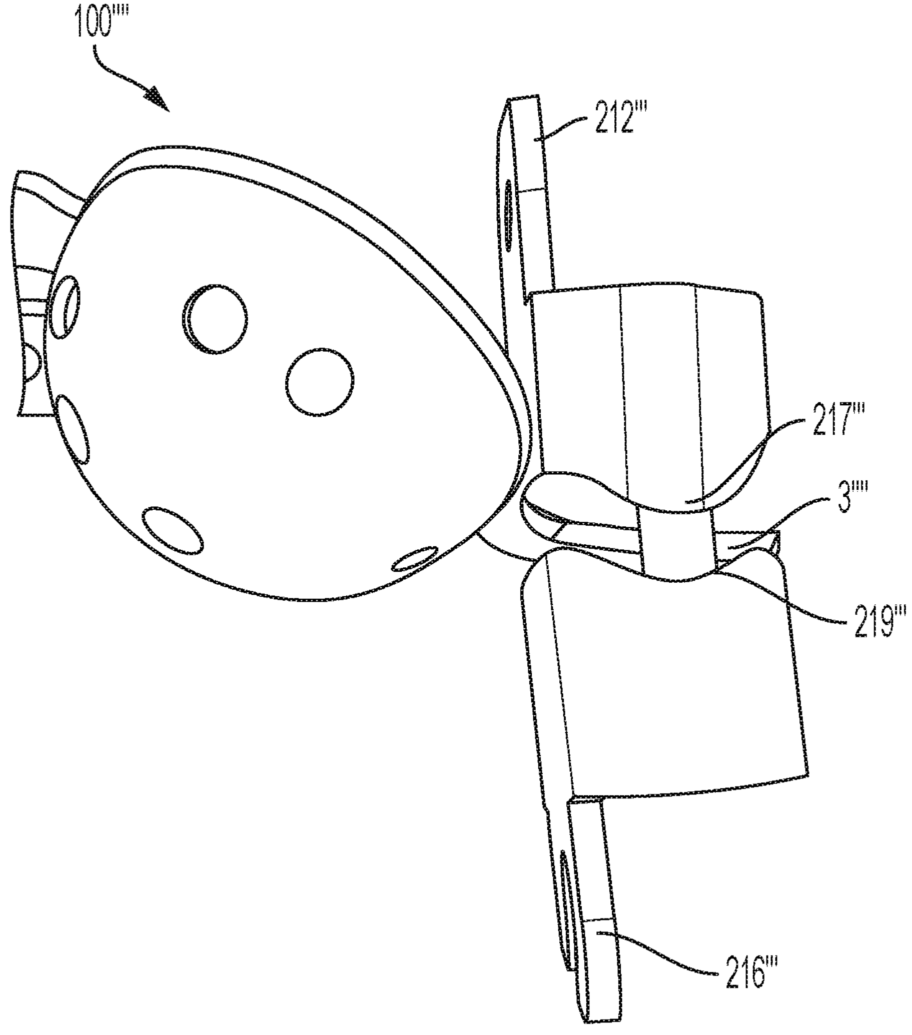
FIG. 12A is a perspective view of a caudal flange.

FIG. 12A is an illustration of the modification tool 206''' with a portion of an implant 100'''' of a silicon or plastic material for illustrative purposes. As can be seen in FIG. 12A, a portion of a caudal flange 3'''' is placed between the upper jaw surface 217''' and the lower jaw surface 219''', so that upon reception of a force, the upper jaw surface 217''' and the lower jaw surface 219''' can move towards each other and bend the portion of the caudal flange 3''''.

Figure 12B:
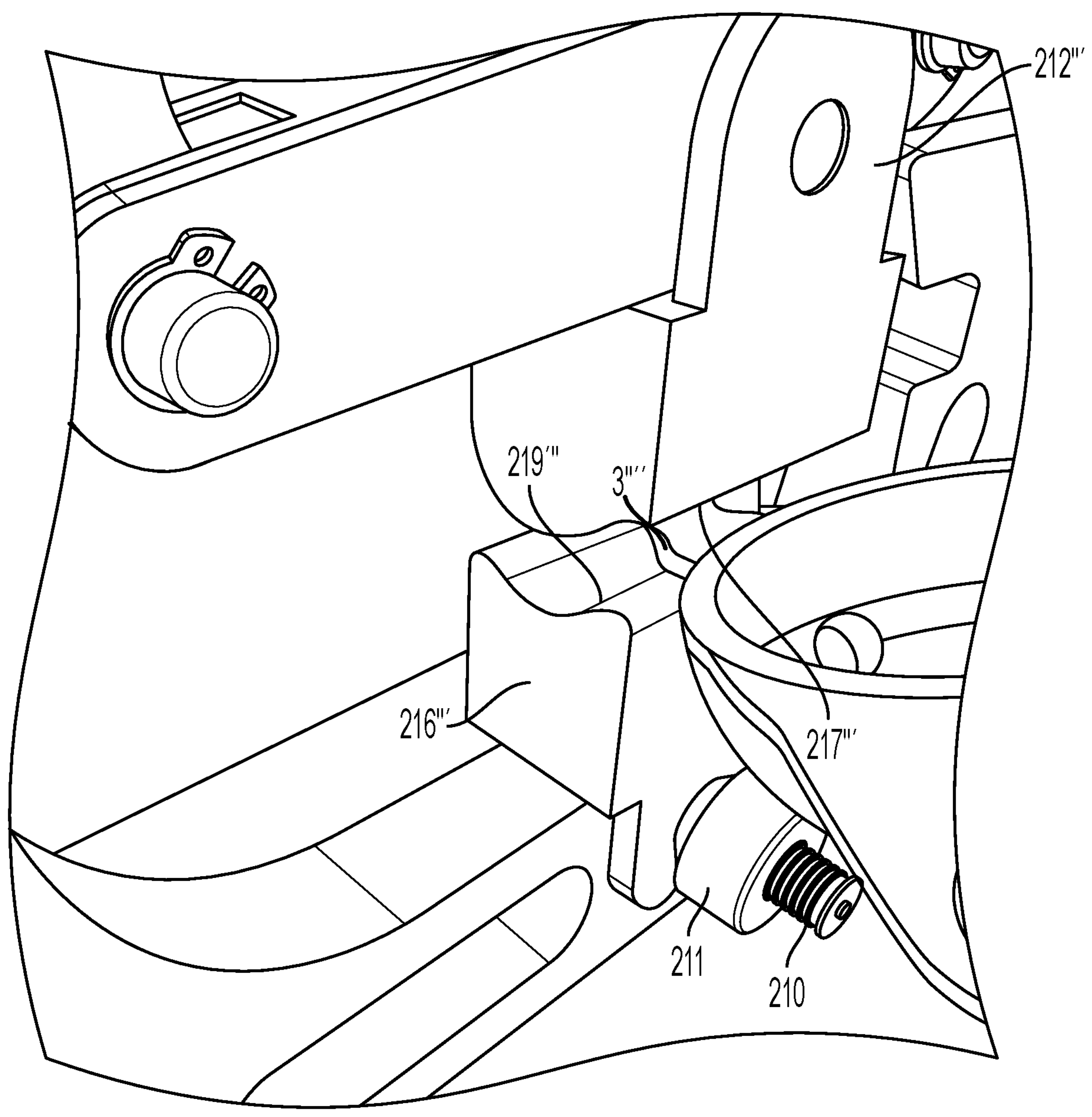
FIG. 12B is a perspective view of a caudal flange.

FIG. 12B is an image of the modification tool 206''' with a portion of a fastening bracket 2'''' extending between the upper jaw surface 217''' and the lower jaw surface 219''', with the caudal flange 3'''' configured to be bent by contact between the upper jaw surface 217''' and/or the lower jaw surface 219'''.

The described embodiments and examples of the present disclosure are intended to be illustrative rather than restrictive, and are not intended to represent every embodiment or example of the present disclosure. While the fundamental novel features of the disclosure as applied to various specific embodiments thereof have been shown, described and pointed out, it will also be understood that various omissions, substitutions and changes in the form and details of the devices illustrated and in their operation, may be made by those skilled in the art without departing from the spirit of the disclosure. For example, it is expressly intended that all combinations of those elements and/or method steps which perform substantially the same function in substantially the same way to achieve the same results are within the scope of the disclosure. Moreover, it should be recognized that structures and/or elements and/or method steps shown and/or described in connection with any disclosed form or embodiment of the disclosure may be incorporated in any other disclosed or described or suggested form or embodiment as a general matter of design choice. Further, various modifications and variations can be made without departing from the spirit or scope of the disclosure as set forth in the following claims both literally and in equivalents recognized in law.

The invention claimed is:

1. A modification device, the modification device comprising:

a base configured to contact a supporting surface;

a handle configured to receive a force; and a modification tool between the handle and the base, wherein the handle is configured to provide a modification force to the modification tool, and wherein the modification tool is configured to receive the modification force and configured to provide the modification force to a portion of an implant, wherein the modification tool comprises a modification opening, wherein the modification opening is configured for a portion of the implant to pass therethrough, wherein the modification tool comprises a movable surface and a fixed surface, wherein the handle is configured to move the movable surface nearer or further from the fixed surface between a modification opening closed configuration and a modification opening open configuration.

2. The device of claim 1, wherein the modification tool is a cutting device.

3. The device of claim 1, wherein the modification tool is a bending device.

4. The device of claim 1, further comprising the implant, wherein the portion of the implant is a fastening bracket of the implant.

5. The device of claim 1, further comprising the implant, wherein the portion of the implant is a caudal flange of the implant.

6. The device of claim 5, wherein the modification tool is dimensioned for the caudal flange.

7. The device of claim 1, wherein the handle is configured to be removable from the modification device without the use of tools.

8. The device of claim 1, wherein the modification tool is configured to be removable from the modification device without the use of tools.

9. The device of claim 1, wherein the modification device comprises a modification device upper opening configured, wherein the modification device upper support is configured to extend through the modification device upper opening, wherein the base comprises a modification device lower support, wherein the modification device comprises a modification device lower slot, and wherein the modification device lower support is configured to extend through a portion of the modification device lower slot.

10. A method of modifying a portion of an implant, the method comprising:

placing a portion of the implant through a modification opening of a modification device of claim 1; and moving a handle of the modification device to provide a modification force to a portion of an implant.

11. The method of claim 10, wherein the modification tool is a cutting device.

12. The method of claim 10, wherein the modification tool is a bending device.

13. The method of claim 10, wherein the portion of the implant is a fastening bracket of the implant.

14. The method of claim 13, wherein the modification tool is dimensioned for the fastening bracket.

15. The method of claim 10, wherein the portion of the implant is a caudal flange of the implant.

16. The method of claim 15, wherein the modification tool is dimensioned for the caudal flange.

17. A method of sterilizing a modification device of claim 1, the method comprising:

removing the modification tool from between the handle and the base;

removing the handle from the modification device;

separating the base into two base pieces;

placing the modification tool, the handle, and the base pieces into a sterilization basket; and exposing the modification tool, the handle, base pieces and the sterilization basket to a sterilizing procedure.

18. The method of claim 17, wherein a size of the modification device in an assembled configuration is larger than a volume of the sterilization basket.

19. The method of claim 17, wherein the handle is configured to be removable from the modification device without the use of tools.

20. The method of claim 17, wherein the modification tool is configured to be removable from the modification device without the use of tools.

* * * * *